US012300119B2

(12) United States Patent
Hipsley et al.

(10) Patent No.: US 12,300,119 B2
(45) Date of Patent: May 13, 2025

(54) OCULAR SIMULATED CAMERA ASSISTED ROBOT FOR LIVE, VIRTUAL OR REMOTE EYE SURGERY TRAINING APPARATUS AND METHOD

(71) Applicant: Ace Vision Group, Inc., Newark, CA (US)

(72) Inventors: AnnMarie Hipsley, Newark, CA (US); David Austin Neal, Newark, CA (US)

(73) Assignee: Ace Vision Group, Inc., Newark, CA (US)

( * ) Notice: Subject to any disclaimer, the term of this patent is extended or adjusted under 35 U.S.C. 154(b) by 0 days.

(21) Appl. No.: 17/890,531

(22) Filed: Aug. 18, 2022

(65) Prior Publication Data

US 2023/0142530 A1 May 11, 2023

Related U.S. Application Data

(60) Provisional application No. 63/235,574, filed on Aug. 20, 2021.

(51) Int. Cl.
*G09B 23/32* (2006.01)
*G09B 23/30* (2006.01)

(52) U.S. Cl.
CPC ............ *G09B 23/32* (2013.01); *G09B 23/306* (2013.01)

(58) Field of Classification Search
CPC .............................. G09B 23/32; G09B 23/306
See application file for complete search history.

(56) References Cited

U.S. PATENT DOCUMENTS

| 2009/0111081 A1 | 4/2009 | Nylen |
| 2015/0025681 A1 | 1/2015 | Riek |
| 2019/0221138 A1 | 7/2019 | Kirchhoff et al. |
| 2020/0365058 A1 | 11/2020 | Kirchhoff et al. |
| 2023/0067625 A1 | 3/2023 | Hipsley et al. |

OTHER PUBLICATIONS

Ramos, L. et al. (May 12, 2017). "Robotic Face to Simulate Humans Undergoing Eye Surgery," 30th Florida Conference on Recent Advances in Robotics, pp. 1-6, XP093003207, Retrieved from the Internet: URL:https://public.eng.fau.edu/design/fcrar2017/papers/RoboticFaceSimulating.pdf [retrieved on Nov. 29, 2022.

Yang, S. et al. (2018). "Techniques for robot-aided intraocular surgery using monocular vision." The International Journal of Robotics Research, 37(8), 931-952. XP093003190, Sage, ISSN: 0278-3649, DOI: 10.1177/0278364918778352.

*Primary Examiner* — Robert P Bullington

(74) *Attorney, Agent, or Firm* — Mintz Levin Cohn Ferris Glovsky and Popeo, P.C.

(57) ABSTRACT

A method for ocular simulated camera assisted robot training is provided. In some implementations, the method includes initializing, by a processor, a robotics assembly. The method further includes connecting, by the processor, to one or more computing devices. The method further includes operating, by the processor, the robotics assembly. The method further includes simulating, by the processor, an eye movement of a human or animal. The method further includes operating, by the processor, a laser to perform a determined exercise on an eye of the robotics assembly. Related systems, methods, and articles of manufacture are also described.

22 Claims, 42 Drawing Sheets

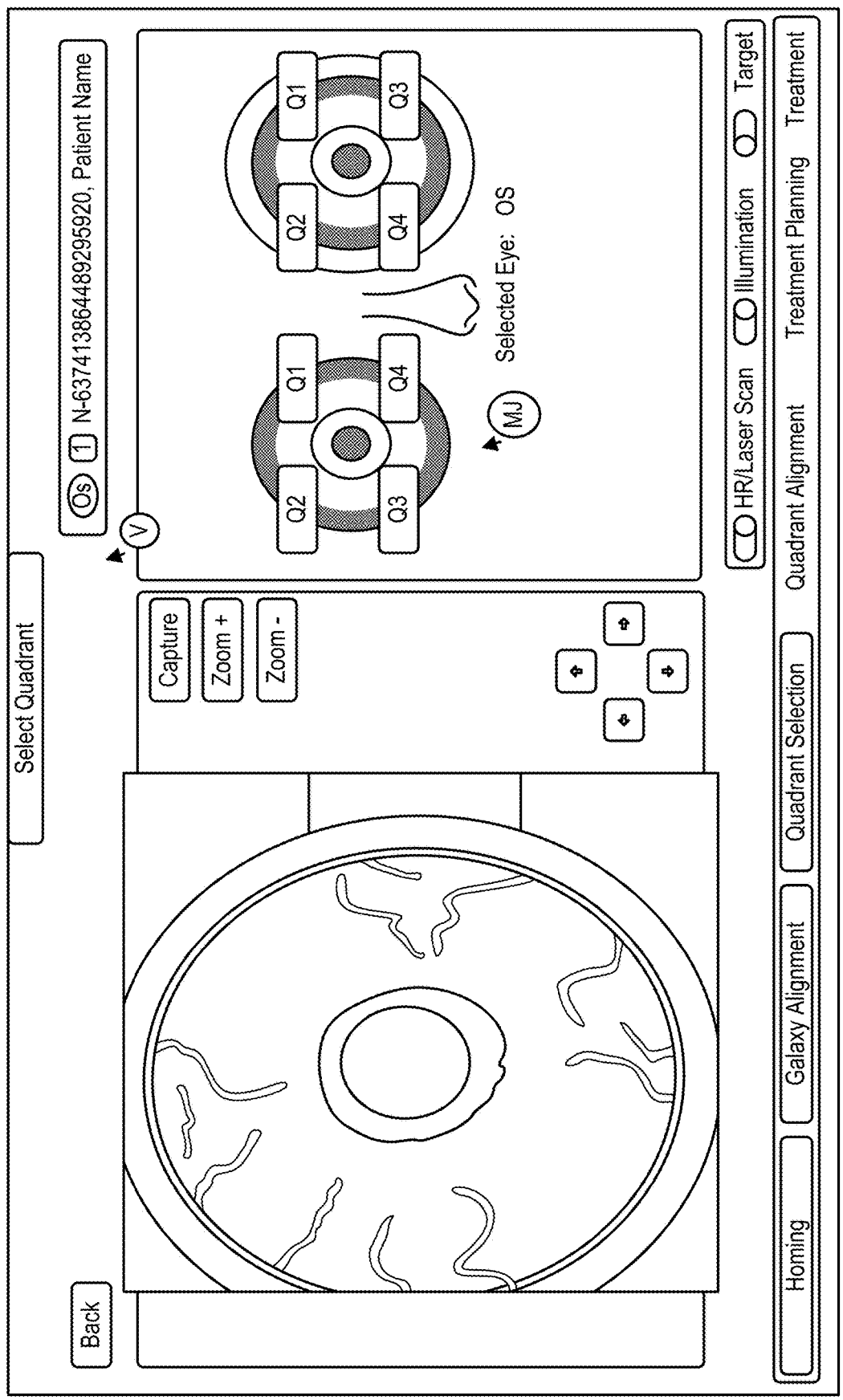
FIG. 10E1

Use Case for Cataract LASIK:

Use Case Laser Scleral Microporatiom

OCULAR SIMULATED CAMERA ASSISTED ROBOT FOR LIVE, VIRTUAL OR REMOTE EYE SURGERY TRAINING APPARATUS AND METHOD

CROSS REFERENCE TO RELATED APPLICATION

This application claims the benefit of U.S. Provisional Patent Application No. 63/235,574 filed Aug. 20, 2021, of which is incorporated herein by reference in its entirety and for all purposes.

TECHNICAL FIELD

The subject matter described herein relates to remote eye surgery training, and more particularly, an ocular simulation camera analog robot (OSCAR) for eye surgery training.

BACKGROUND

Laser eye therapies (e.g., surgery) and ophthalmic therapeutics administered in various locations on the eye can require high levels of accuracy and precision to restore natural visual accommodation for better near, intermediate, and distance vision for the more than 1 billion presbyopes who do not currently have a therapeutic solution to treat their condition. Many hours to years of education and training are essential for successful operations, treatments, therapeutics, and the like.

Current surgical training requires experience on either live animals or humans. Animatronic robotic simulations which could mimic the behavior of a live animal or human would provide ability to train surgeons in either a live or remote environment while preserving animal sacrifices and potentially complications in human eyes resulting from early stage surgical experience.

It is therefore desirable to provide improved systems, devices and methods for performing simulations ocular procedures that included but not limited to robotic ocular structures including the cornea, iris, trabecular meshwork, retina, ciliary muscle, lens, zonules, sclera, and choroid in order to identify, observe, and manipulate critical anatomic structures to perform remote procedures on an eye.

SUMMARY

In some aspects, a method, computer program product and system are provided. In an implementation, a remote eye surgery training system is provided.

The system includes a base plate. The system further includes a faceplate coupled to the base plate. The system further includes a data repository and database which can communicate with a plurality of external inputs. The system can further collect telemetry data and produce outputs to various extremal device. The system can include a controller electronically connected to at least one processor and configured to receive an input to control a position of the eye. The system further includes an eye holder disposed within the face plate. The system further includes an interface board configured to provide an electronic connection between the at least one processor and the eye holder. The system further includes an eye disposed in the eye holder. The system further includes a user interface configured to receive a user input to control a movement of the eye. The system further includes at least one processor coupled to the base plate. The at least one processor and/or memory, configured to perform operations including initialize a position of the eye. The at least one processor further configured to connect to one or more computing devices. The at least one processor further configured to control, by the one or more computing devices, the position of the eye. The at least one processor further configured to simulate an eye movement of a human or animal. The at least one processor further configured to perform a laser procedure on the eye to simulate a plurality of eye movements both normal and abnormal. The simulator is able to move in anatomical extremes which may not be possible in reality.

In some variations of the system, the system further includes an "iris" shutter which is mechanically responsive to various stimulation and light iterations. The system further can be mechanically fixed to a plurality of iris sizes. The system further is designed for contrast to allow the eye to work parallel to the function of a human or animal eye. The system further is designed so as to simulate a normal human eye function.

The system includes a "blink" function to mechanically simulate normal eye blinking which allows for the gathering of eye data as close to reality as possible.

In some variations of the system, the system further includes a laser. The eye holder includes a suction cup controlled by the user interface. The eye holder may include an apparatus that initializes, monitors, adjusts, and measures intraocular pressure inside the eye.

In one aspect, a method is provided. The method includes initializing, by a processor, a robotics assembly. The method further includes connecting, by the processor, to one or more computing devices. The method further includes operating, by the processor, the robotics assembly. The method further includes simulating, by the processor, a plurality of human or animal eye movements. The method further includes operating, by the processor, a laser to perform a determined exercise on an eye of the robotics assembly.

In some variations of the method, the determined exercise may include a plurality of simulated eye procedures and surgeries including but not limited to simulated cataract surgery, a simulated Lasik surgery, a simulated retina treatment, a simulated implantation procedure, a vision treatment, or an eye measurement. Simulating the eye movement may include controlling the movement via a user interface hardware commands, remote commands, or voice commands. Initializing the robotics assembly may include installing an eye into an eye holder of the robotics assembly. The eye may include one of a glass eye, a wooden eye, a cadaver eye, a phantom material and an artificial eye. The user interface may include one or more modes to simulate a real human or animal eye movement or an extreme movement that is abnormal. The one or more modes may include a directed gaze mode, a flutter mode, nystagmus mode, a saccadic mode, microsaccades mode, tremor mode and drift mode, animal mode and a human mode. The eye holder may be configured to change a pressure in the eye and/or change a position of the eye within the eye holder. The method may further include tracking a position of the eye. The method may further include verifying, in response to the tracking, the position matches a target position. The method may further include the fixation of the eye to a particular target.

Implementations of the current subject matter can include systems and methods consistent with the present description, including one or more features as described, as well as articles that comprise a tangibly embodied machine-readable medium operable to cause one or more machines (e.g., computers, etc.) to result in operations described herein. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an enterprise resource planning (ERP enterprise resource planning software) system or other business software solution or architecture, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 10E1 depicts an example graphical user interface for interacting with the remote eye surgery training system, in accordance with some example implementations;

When practical, similar reference numbers denote similar structures, features, or elements.

DETAILED DESCRIPTION

As noted above and as detailed below, embodiments of methods and devices described herein include a number of aspects which may be usefully employed in combination or separately, and which may be advantageously used to treat a range of disease conditions, both of the eye and other regions of the body. At least some of the examples described in particular detail focus on treatment of conditions of the eye, such as the treatment of age-related glaucoma, cataract formation, and other age-related ocular diseases such as age-related macular degeneration, or the like.

In particular, embodiments described herein relate to a hardware, software, firmware, computational circuit, or other system solution used for remote eye surgery training. The training system may provide human-like and/or animal-like movement of the animatronics which may be species dependent. Such movement may improve surgery training by at least providing more realistic eye movement during surgery than a cadaver or other eye simulation.

Figure 1:
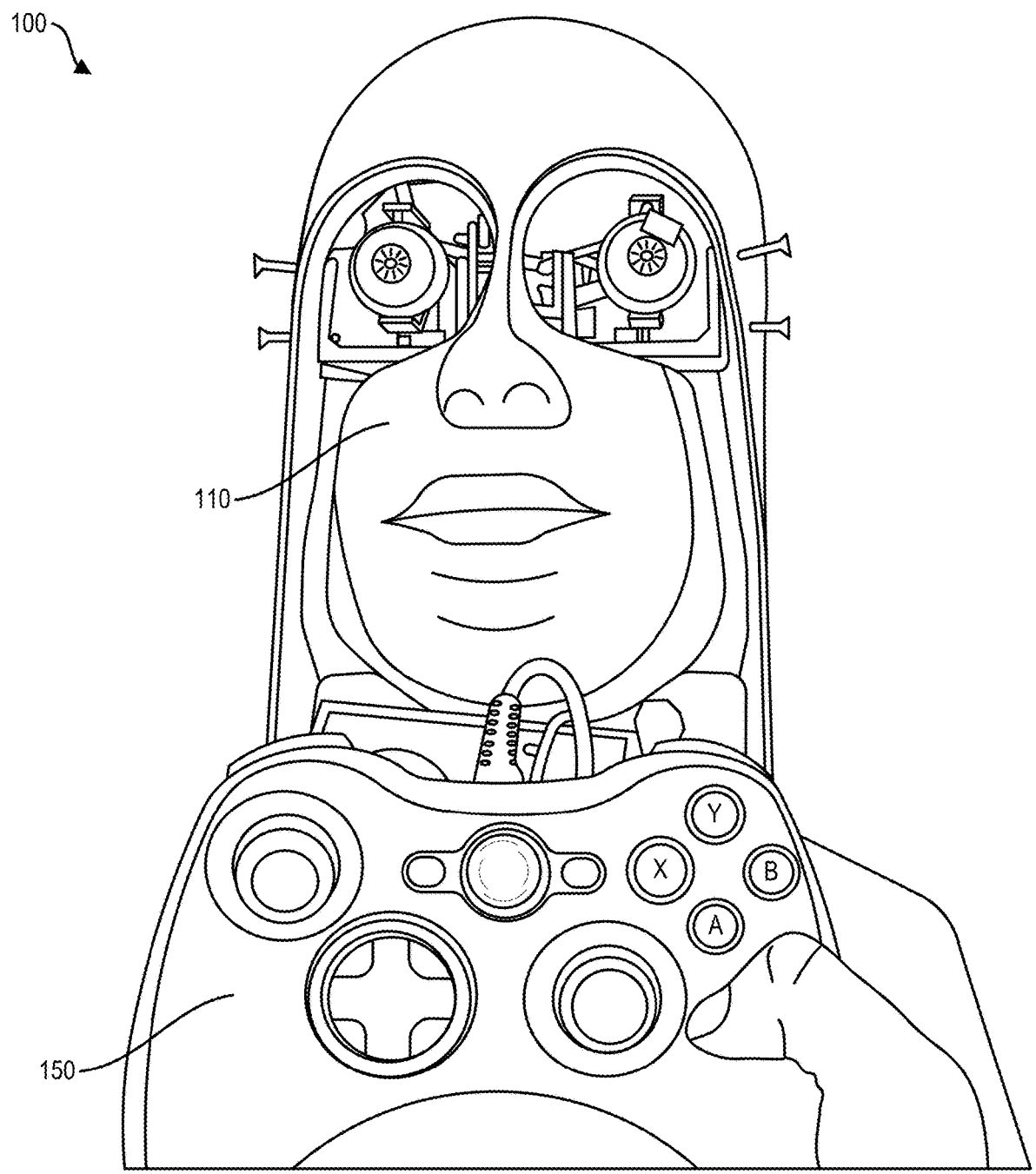
FIG. 1 depicts a system for remote eye surgery training, in accordance with some example implementations.

FIG. 1 depicts a system 100 for remote eye surgery training, in accordance with some example implementations. As shown, the system 100 includes a robotics assembly 110 and a controller 150. In some aspects, the controller 150 may be configured to control movement of at least some portions (e.g., one or more eyes) of the robotics assembly 110. The controller 150 may include a joystick, a keypad, a mouse, a gaming controller, a touchscreen, or the like.

Figure 2A:
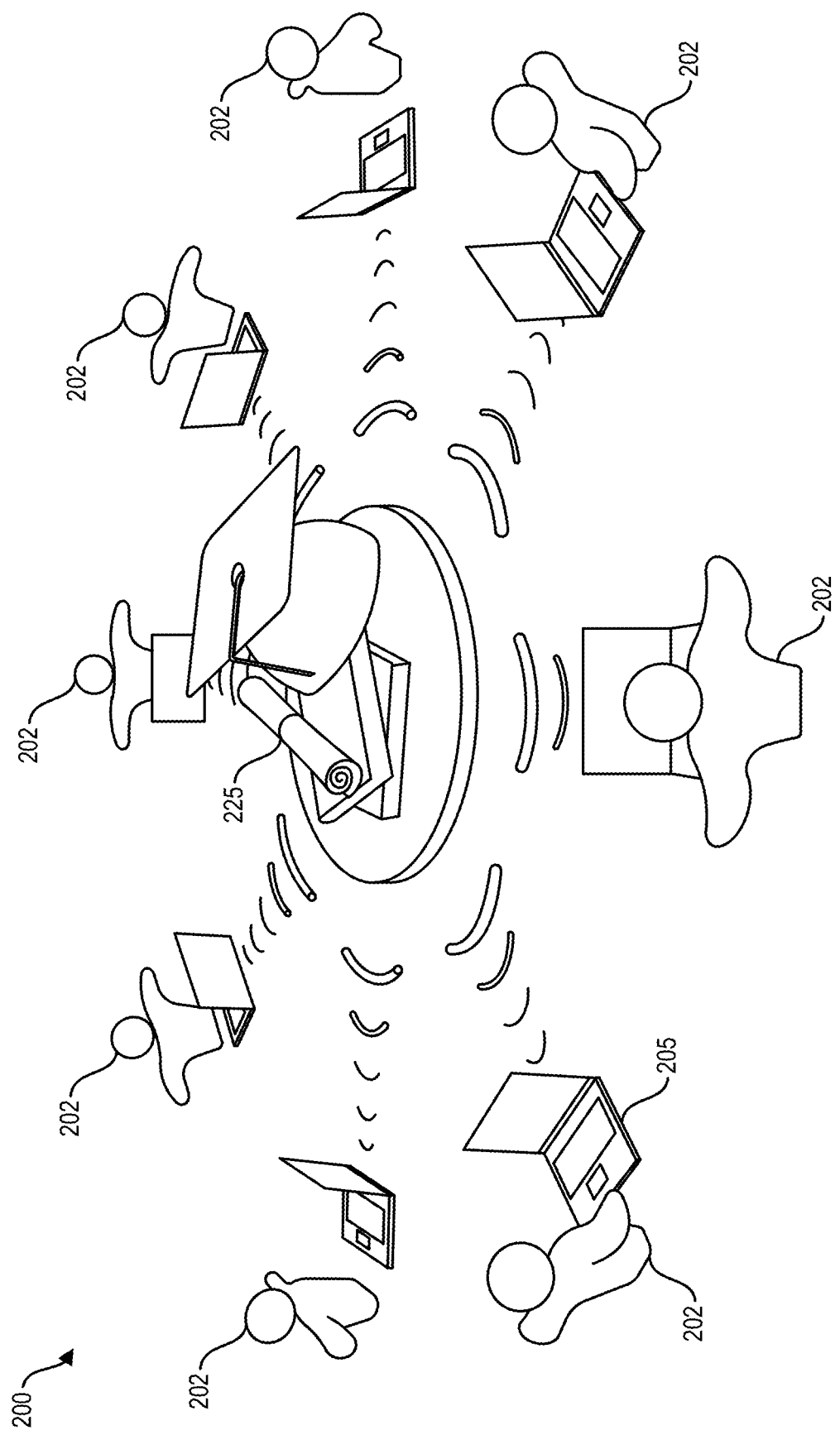
FIG. 2A depicts a remote training environment, in accordance with some example implementations.

FIG. 2A depicts a remote training environment 200, in accordance with some example implementations. As shown, the example training environment 200 includes at least one user 202 in communication with a server 225. In some aspects, the server 225 may host a webinar, presentation, virtual wetlab, or the like. The users 202 may be associated with a client device 205 which is logged into the presentation of the server 225. In some aspects, the server 225 may also be in communication with the robotics assembly 110 and may provide remote controls for the robotics assembly 110. In some implementations, the client device 205 may also include controls configured to move portions of the robotics assembly 110. In some aspects, remote training for the users 202 may be done using a remote demo device (e.g., robotics assembly 110) in communication with the server 225. The example training environment 200 may beneficially allow training seminars to be held with multiple users 202 which can be completed at the user's 202 convenience.

Figure 2B:
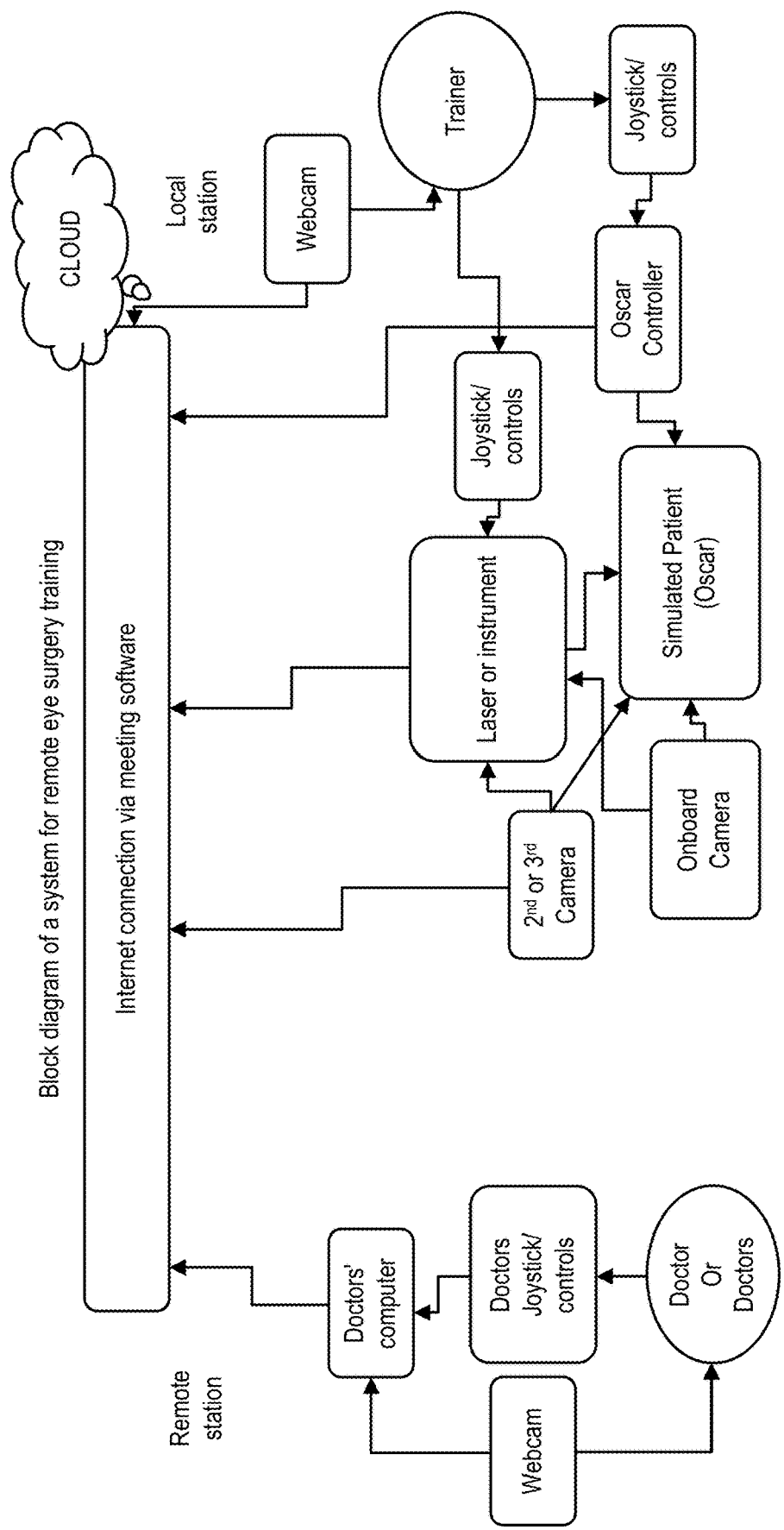
FIG. 2B depicts a block diagram of a system for remote eye surgery training, in accordance with some example implementations.

FIG. 2B depicts a block diagram of a system 250 for remote eye surgery training, in accordance with some example implementations. FIG. 2B shows example connections between users (e.g., users 202) and computing devices (e.g., client device 205, server 225, robotics assembly 110, or the like). As shown, all users and devices are connected, either directly or indirectly, with a wireless connection (e.g., Internet connection) via commercially available videoconferencing software. While an Internet connection is shown, the connection between users and devices may be wired or accomplish with another wireless technology. While certain users and devices are shown, other users and other devices are also possible. The videoconferencing software may include any video telephonic, chat, holographic, or any other type of videoconferencing or meeting software.

Figure 2C:
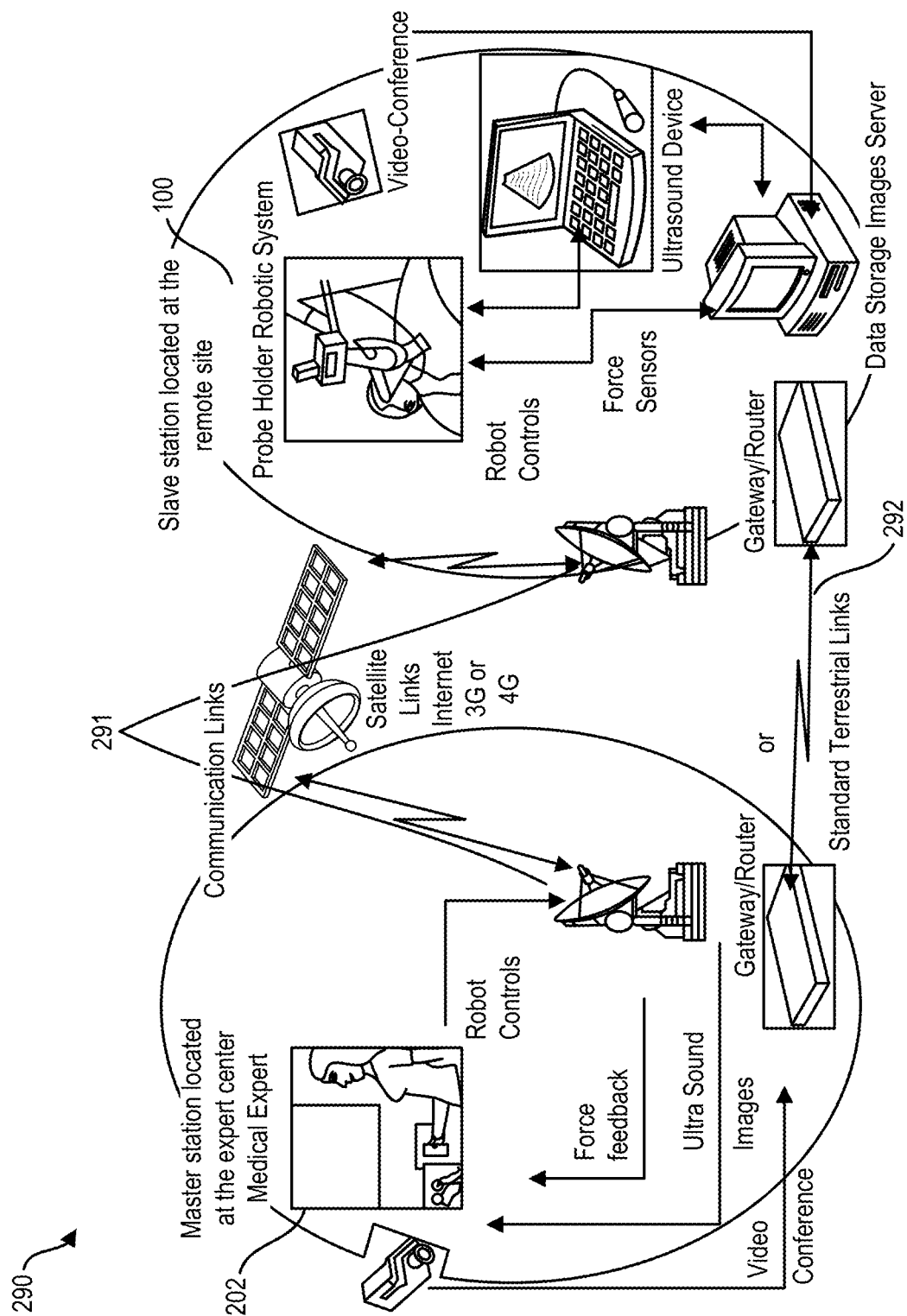
FIG. 2C depicts a diagram for an example wireless network, in accordance with some example implementations.

FIG. 2C depicts a diagram for an example wireless network 290, in accordance with some example implementations. As shown, a remote robotic system (e.g., system 100) can operate through a plurality of network links through communication with a medical expert/professional (e.g., user 202 via client device 205, server 225, or the like). The plurality of network links may include broadband network links such as integrated services digital network (ISDN), local area networks (LANs), and dedicated T-1 lines the Internet and or low broad bandwidth links. As further shown in FIG. 2C the wireless network 290 includes a satellite link 291, a terrestrial link 292, to facilitate communication between the system 100 and the user 202. Teleoperated medical robotic systems (e.g., system 100) may allow procedures such as surgeries, treatments, and diagnoses to be conducted across short or long distances while utilizing wired and/or wireless communication networks. Further, teleoperated medical robotic systems may provide an operating room environment to remote real-time surgical consultation. The connection permitted video and audio teleconferencing may support real-time consultation as well as the transmission of real-time images and store-and-forward images for observation by a consultant panel.

For example the user 202 may control operation of the system 100 through the wireless network 290. Advanced control techniques including robust and adaptive control are particularly relevant to bilateral teleoperation systems (e.g. system 100). Robust control is capable of preserving stability and performance despite uncertainties or disturbances affecting the system. In general, adaptive control has the ability to adapt to controlled systems with unknown or varying parameters where an adaptive control scheme is proposed to deal with both dynamic and kinematic uncertainties regarding a remote manipulation system while communication delays or errors are also taken into account.

Figure 2D:
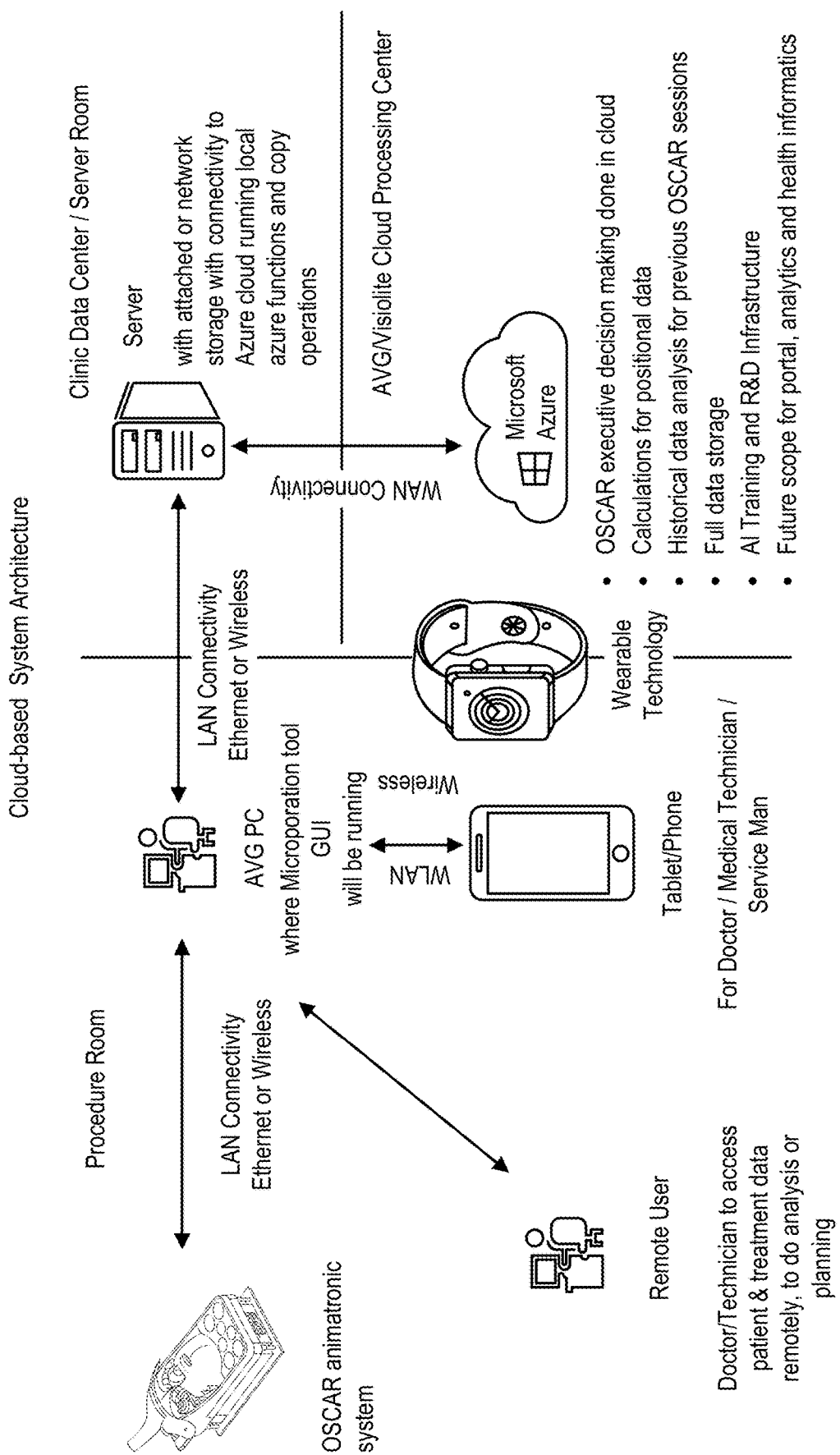
FIG. 2D depicts a cloud based system architecture, in accordance with some example implementations.

FIG. 2D depicts a cloud based system architecture, in accordance with some example implementations. As shown, a cloud processing center may control executive decisions of the robotics assembly 110, perform calculations for positional data of the robotics assembly 110 (e.g., positional data of the eye 506), perform historical data analysis of previous training sessions with the robotics assembly 110, store data, perform artificial intelligence (AI) training, provide research and development infrastructure, and provide analytics and health informatics.

Figure 3A:
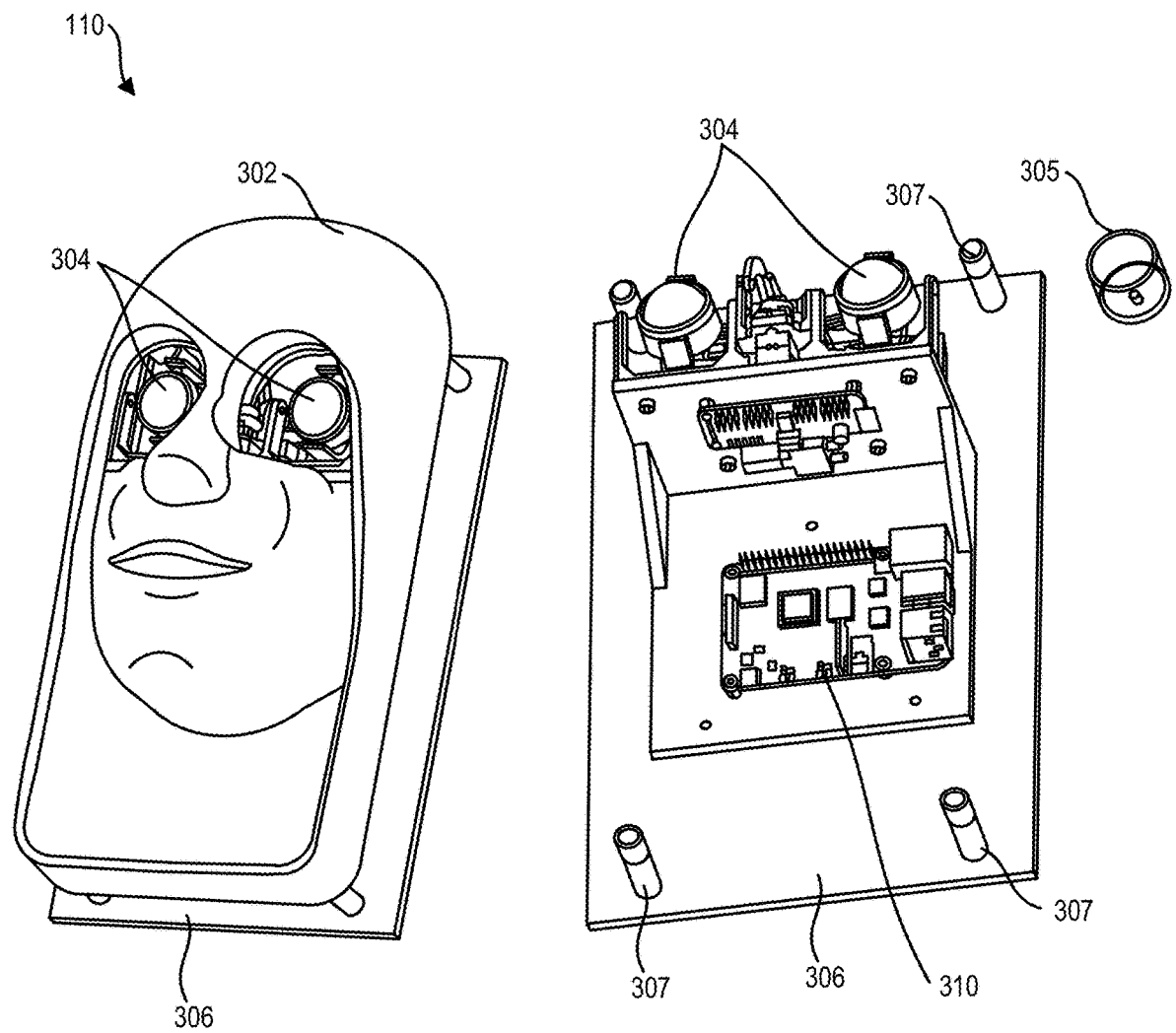
FIG. 3A is a perspective view of a robotics assembly, in accordance with some example implementations.
Figures 3B, 3C, 3D, 3E:
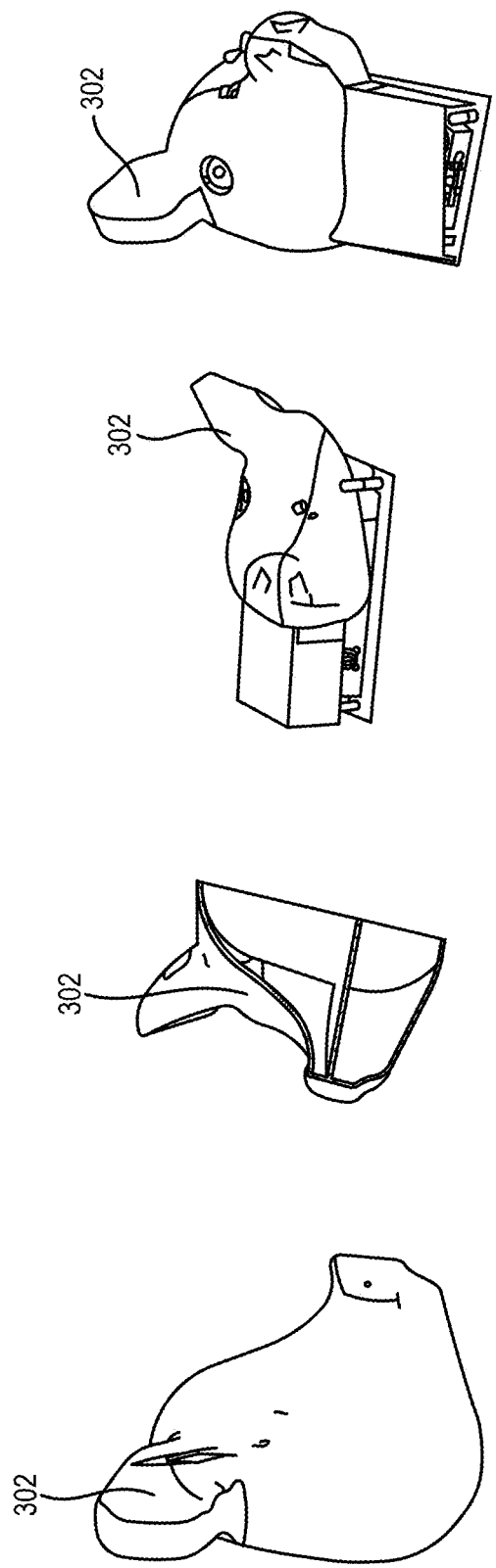
FIGS. 3B-3E depict example profile views of a faceplate having an animal face, in accordance with some example implementations.

FIG. 3A is a perspective view of the robotics assembly 110, in accordance with some example implementations. As shown, the robotics assembly 110 includes a faceplate 302, a robotic eye assembly 304, a base plate 306, and a processor 310. In some aspects, the robotics assembly 110 may include an alternate example eye holder 305. In some embodiments, the faceplate 302 may couple to the base plate 306 via connection pins 307.

While the faceplate 302 is shown with a human face, the faceplate 302 may be removable and molded in the shape of any species of animal (e.g., pig, monkey, etc.) or a human. FIGS. 3B-3E depicts example profile views of a faceplate 302 having an animal (e.g., pig) faceplate 302.

Figure 4A:
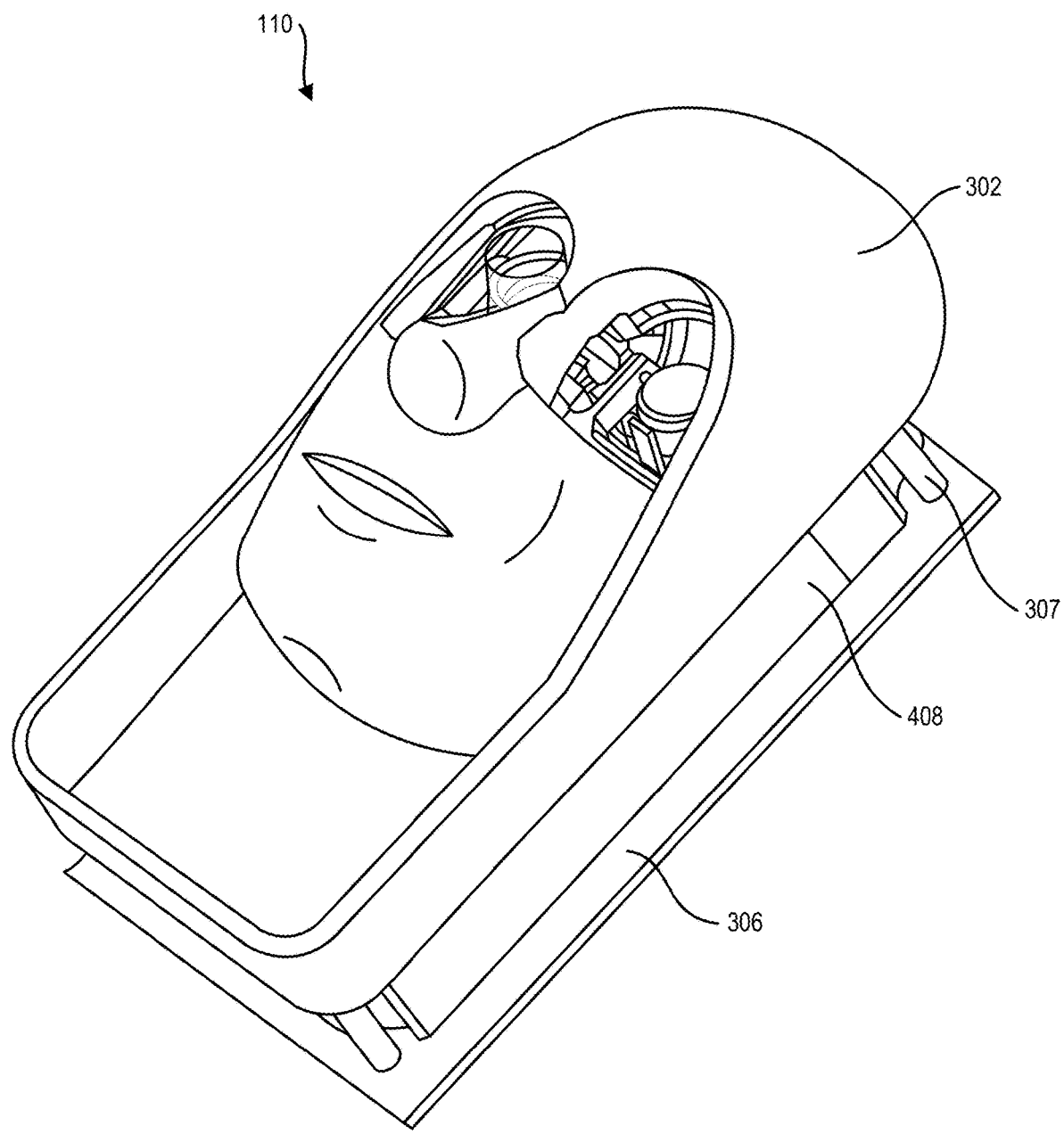
FIGS. 4A-4C depict the example robotics assembly with a shield, in accordance with some example implementations.
Figure 4B:
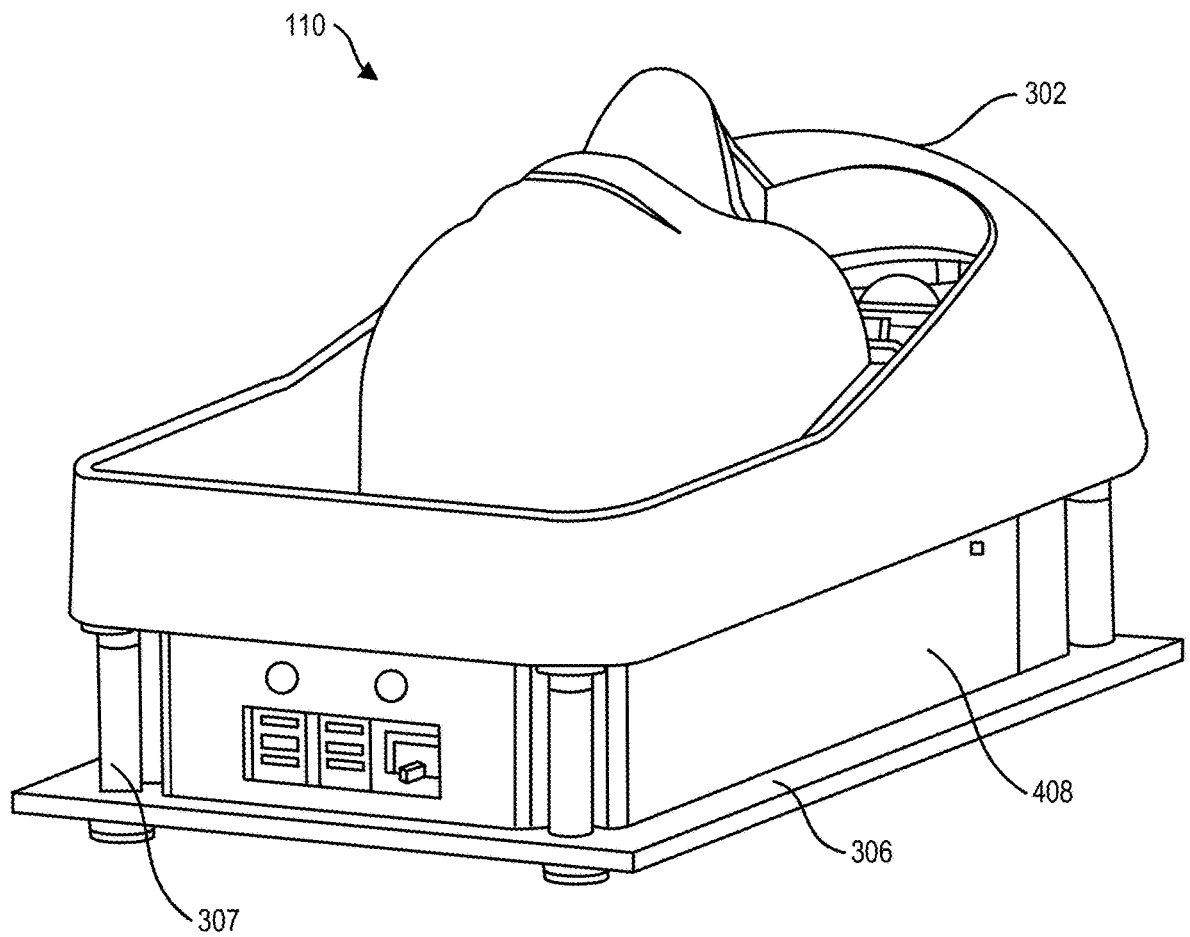
Figure 4C:
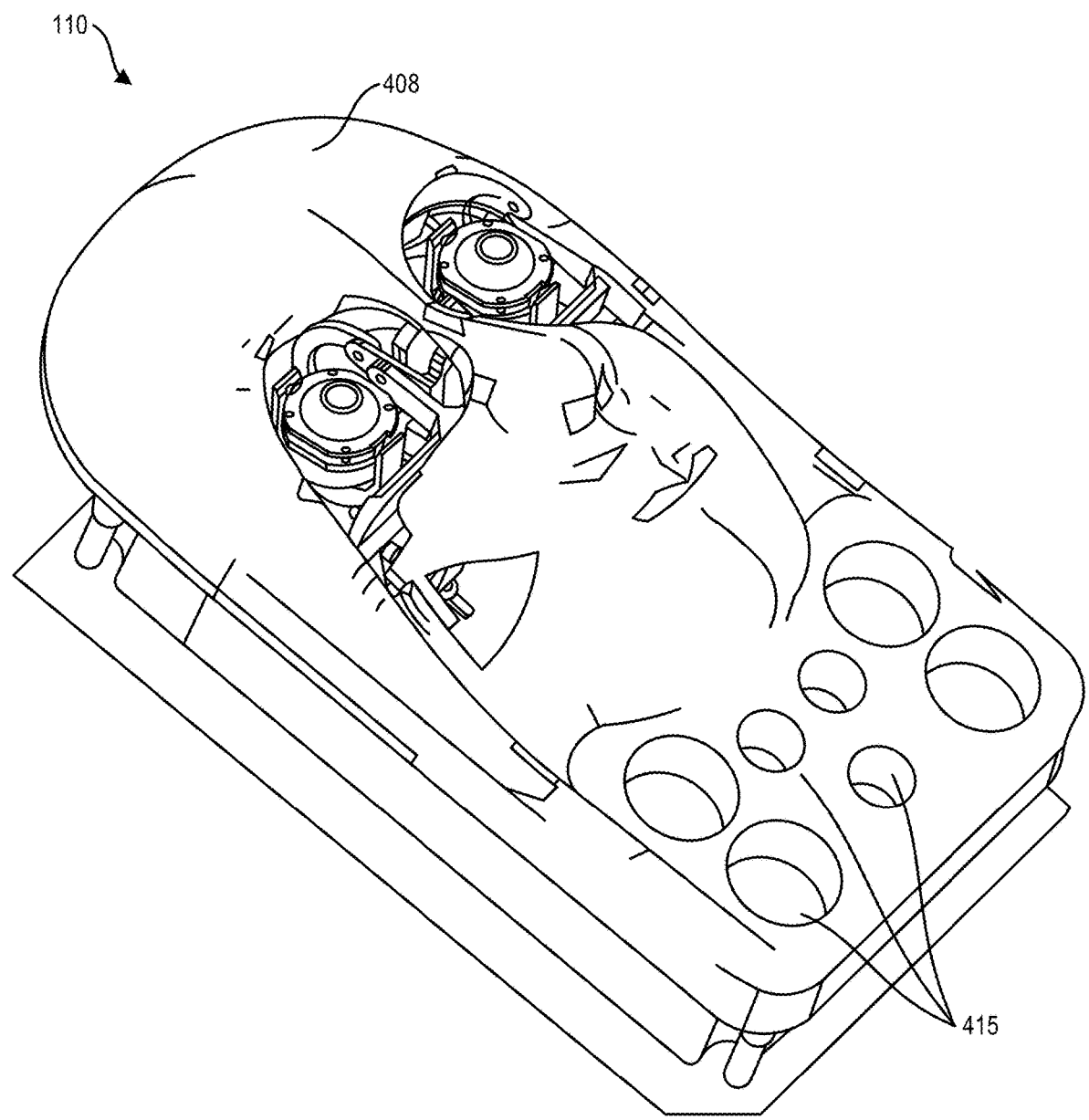

FIG. 4A is a perspective view of the robotics assembly 110 with a shield 408, in accordance with some example implementations. FIG. 4B, is a side view of the robotics assembly 110 with the shield 408, in accordance with some example implementations. FIG. 4C is a perspective view of the robotics assembly 110 with the shield 408. As shown in the example of FIG. 4C, the shield 408 includes recesses 415. In some aspects, the recesses 415 may be configured to hold objects relevant to the robotics assembly 110, an eye surgery training procedure, or the like. For example, the recesses 415 may be sized and configured to hold eye bottles, other eye cups, replacement parts, bottles for eye drops, or the like.

Figure 5A:
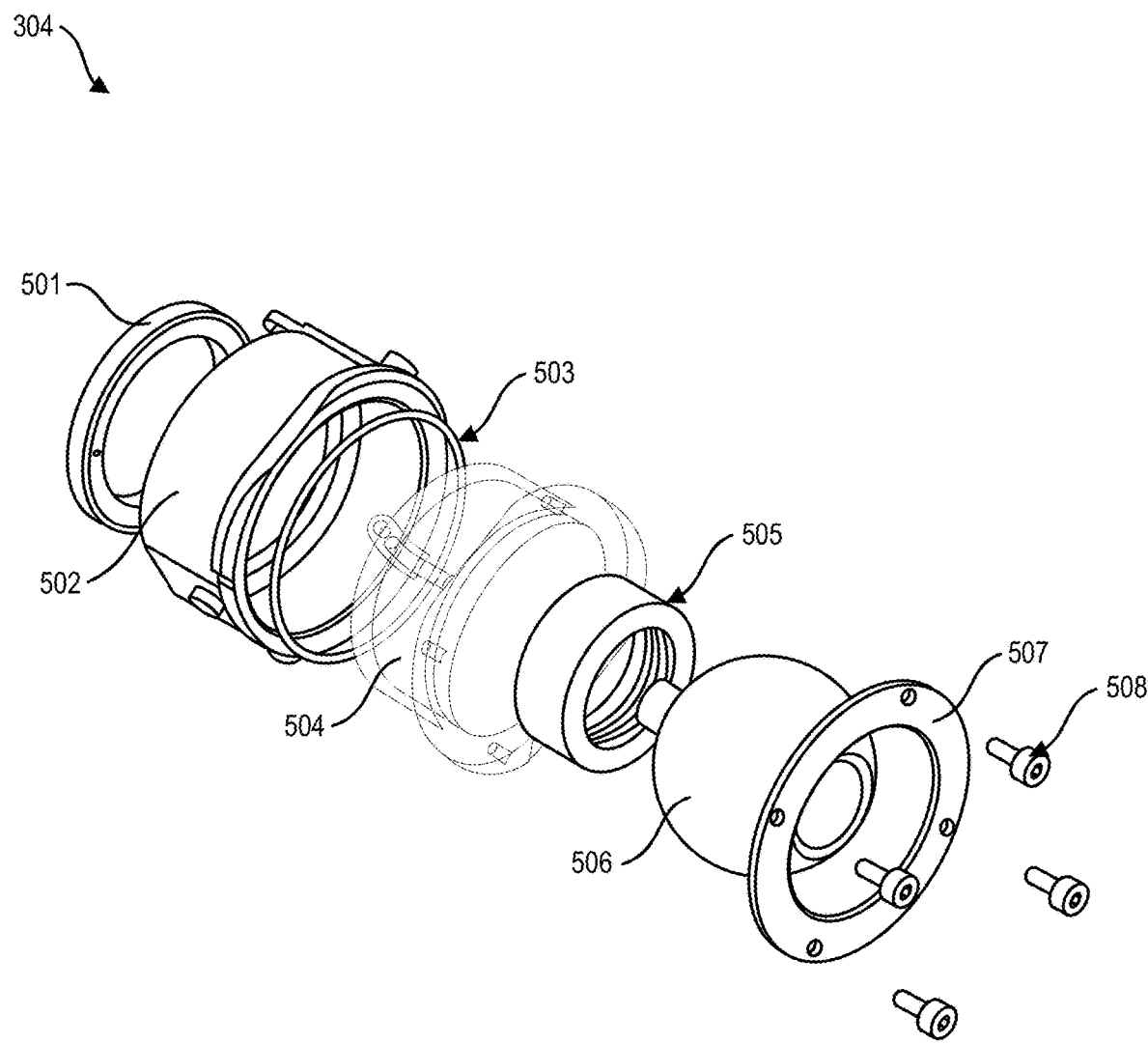
FIG. 5A is an exploded view of a robotic eye assembly, in accordance with some example implementations.

FIG. 5A is an exploded view of an example robotic eye assembly 304, in accordance with some example implementations. As illustrated, the robotic eye assembly 304 can include a retaining ring 501, and eye holder 502, and O ring 503, and eye cup 504, a spacer 505, an eye 506, a clamping ring 507, and clamping screws 508. The retaining ring 501 may be configured to hold the eye cup 504 in position. The retaining ring 501 may have the ability to move the eye cup 504 lower or higher in the eye holder 502. The eye holder 502 may hold the eye cup 504 in position and may translate the movement input from a servo and a linkage to the eye cup 504. The eye holder 502 may include two pivot points on opposite sides for left and right (L/R) movement. The eye holder 502 may include a flange or boss that is the connection point to the linkage to the L/R servo.

The eye holder 502 may include a groove that includes an O-ring (e.g., O-ring 503). The O-ring 503 may be designed to be slightly smaller than the eye cup 504 so that it is held in place. The O-ring 503 may provide tension between the cup 504 and the holder 502 and may be designed to keep the eye cup 504 centered and held in the holder 502. The eye holder 502 may include an apparatus (not shown) that initializes, monitors, adjusts, and measures intraocular pressure inside the eye 506. The apparatus may include a pressure meter, or transducer which is attached, detached or integrated into the apparatus of the holder which measures, meters, monitors and displays the intraocular pressure.

The eye holder 502 may include a lip on the top that is designed to hold a rubber contamination shield (such as a dental dam). This shield may keep liquids away from any animatronics or electronics underneath. The eye cup 504 may be designed to hold the eye 506. The eye 506 may include a glass eye, a wooden eye, a cadaver eye, an artificial eye, an animal (e.g., pig, monkey, etc.) eye, or the like. The eye cup 504 may be configured to have a slightly bigger diameter than a pig eye. The eye cup 504 may include a small pipe attached to the bottom to attach a hose. The eye cup 504 may have a lip on the top so that any liquids will fall off this and land either inside the cup or on the contamination shield. The eye cup 504 may include one or more holes to mount a clamp ring (e.g., clamp ring 507). The clamping ring 507 may be one way to hold the eye 506 in the cup 504 (e.g., the cup 504 is placed in the holder 502). The clamping ring 507 may include a slightly smaller ID than the eye so holding it down with screws (e.g., clamping screws 508) will clamp down on the eye 506 and hold it in position. The eye cup 504 may be made from an easily cleanable material (e.g., silicone, plastic, or the like). When used with a hose connected at the bottom and a spacer (e.g., spacer 505), a vacuum can be applied to the hose and the eye 506 may seal against the spacer 505 and be held in place via vacuum. Accordingly, the eye cup 504 may include a section cup that may change the pressure in the eye 506. In some aspects, an amount of vacuum or section applied to the eye 506, the eye cup 504, or the like may be controlled by a user interface (e.g., GUI 1000). The spacer 505 may hold the eye 506 at a correct height so that all quadrants can be treated (e.g., different length spacers for different shaped eyes may be necessary). For the cadaver eye 506, the optic nerve may stick out 2-6 mm from the eyeball at the bottom. The spacer 505 may include a hole in the middle to allow the optic nerve to stay above the bottom of the cup 504. If not, then the eye 506 may be tilted in the cup 504 and may not allow it to be correctly positioned correctly.

Figure 5B:
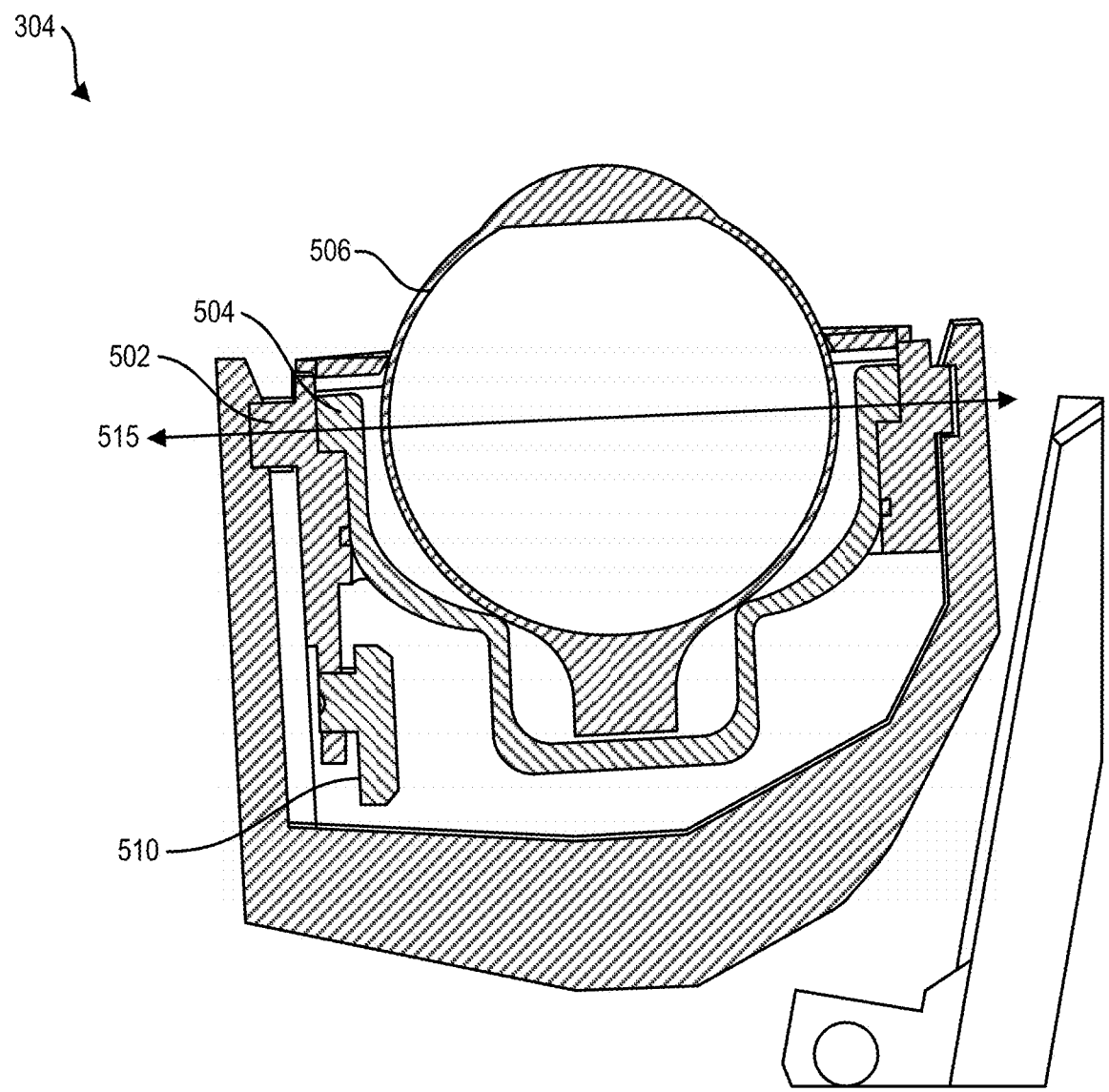
FIG. 5B is a side view of the robotic eye assembly 304, including the eye suction holder mechanism in accordance with some example implementations.
Figure 5C:
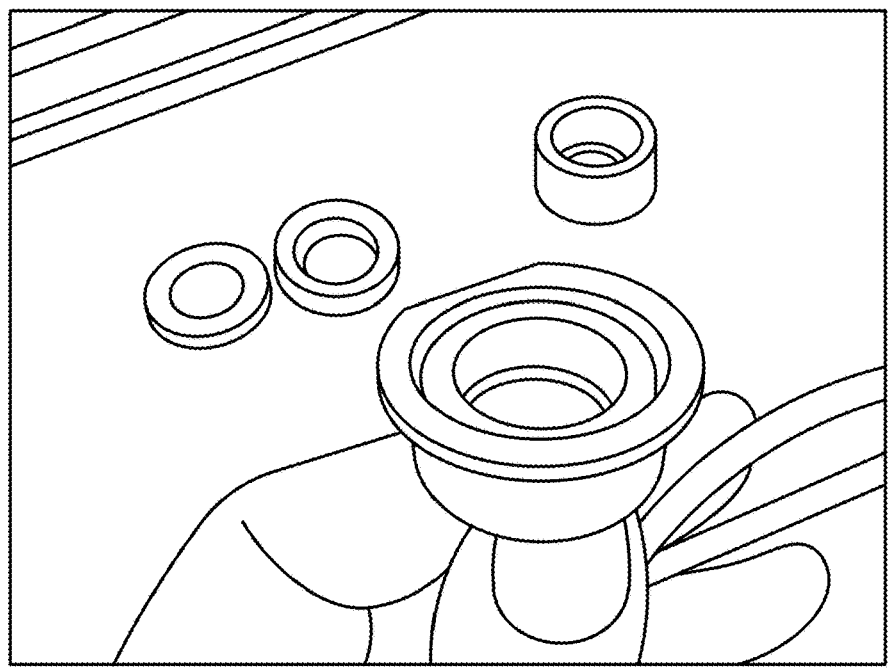
FIGS. 5C and 5D show a suction cup arrangement comprising an eye holder.
Figure 5D:
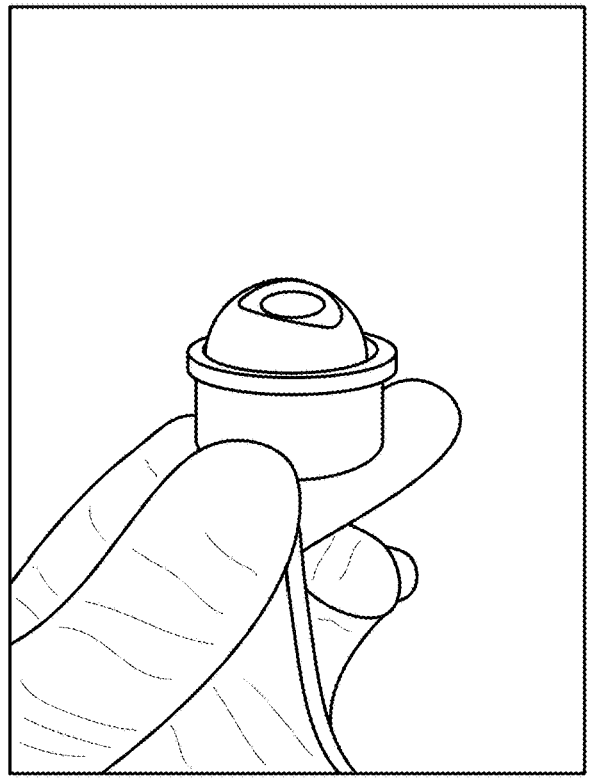

FIG. 5B is a side view of the robotic eye assembly 304, in accordance with some example implementations. As shown, the robotic eye assembly 304 may include a spacer 510. The spacer 510 may be configured to receive an optic nerve or configured to allow the optic nerve to pass through an opening of the robotic eye assembly 304. As further shown, the robotic eye assembly 304 may include a pivot axis 515. In some aspects, the pivot axis 515 may be the same as an axis of the eye 506. In some variations of the system, such as shown in FIGS. 5C and 5D, an eye holder includes a suction cup controlled by the user interface. The eye holder may include an apparatus that initializes, monitors, adjusts, and measures intraocular pressure inside the eye.

Figure 6:
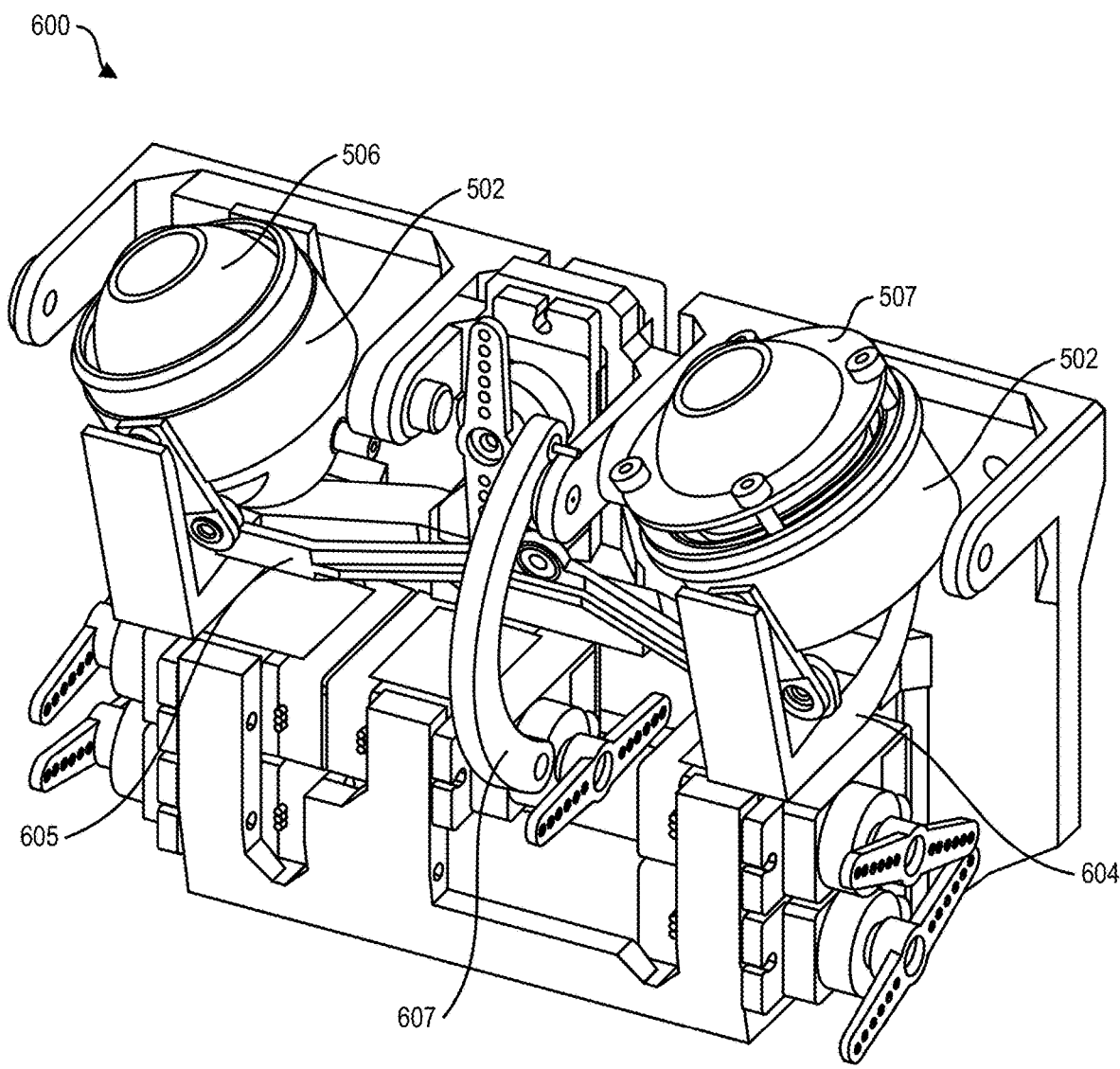
FIG. 6 is a perspective view of an animatronics assembly, in accordance with some example implementations.

FIG. 6 is a perspective view of an animatronics assembly 600, in accordance with some example implementations. As shown, the animatronics assembly 600 includes the eye holder 502, the eye 506, the clamping ring 507, a pivot frame 604, a control arm 605, a Y link 607. The pivot frame 604 may be configured to hold the eyes (e.g., the eye 506) via two pins that are placed in the corresponding holes in the eye holder 502. The pivot frame 604 may provide a base for the eyes to be moved left and right and may be mounted on and other frame that is moved by and up and down servo. The control arm 605 may include a pivot point in the middle that may be coupled to a left/right (L/R) servo. In some aspects, each end of the control arm 605 may be coupled to the eye holders 502 of the left eye 506 and the right eye 506, respectively. The Y link 607 may connect a middle servo and the eye holders 502. The Y link 607 may also be configured to transmit the middle servo movement to a frame of the animatronics assembly 600. Since the frame may be mounted on both sides as a pivot point, when the servo is moved, the eyes then may move upward and/or downward.

Figure 7:
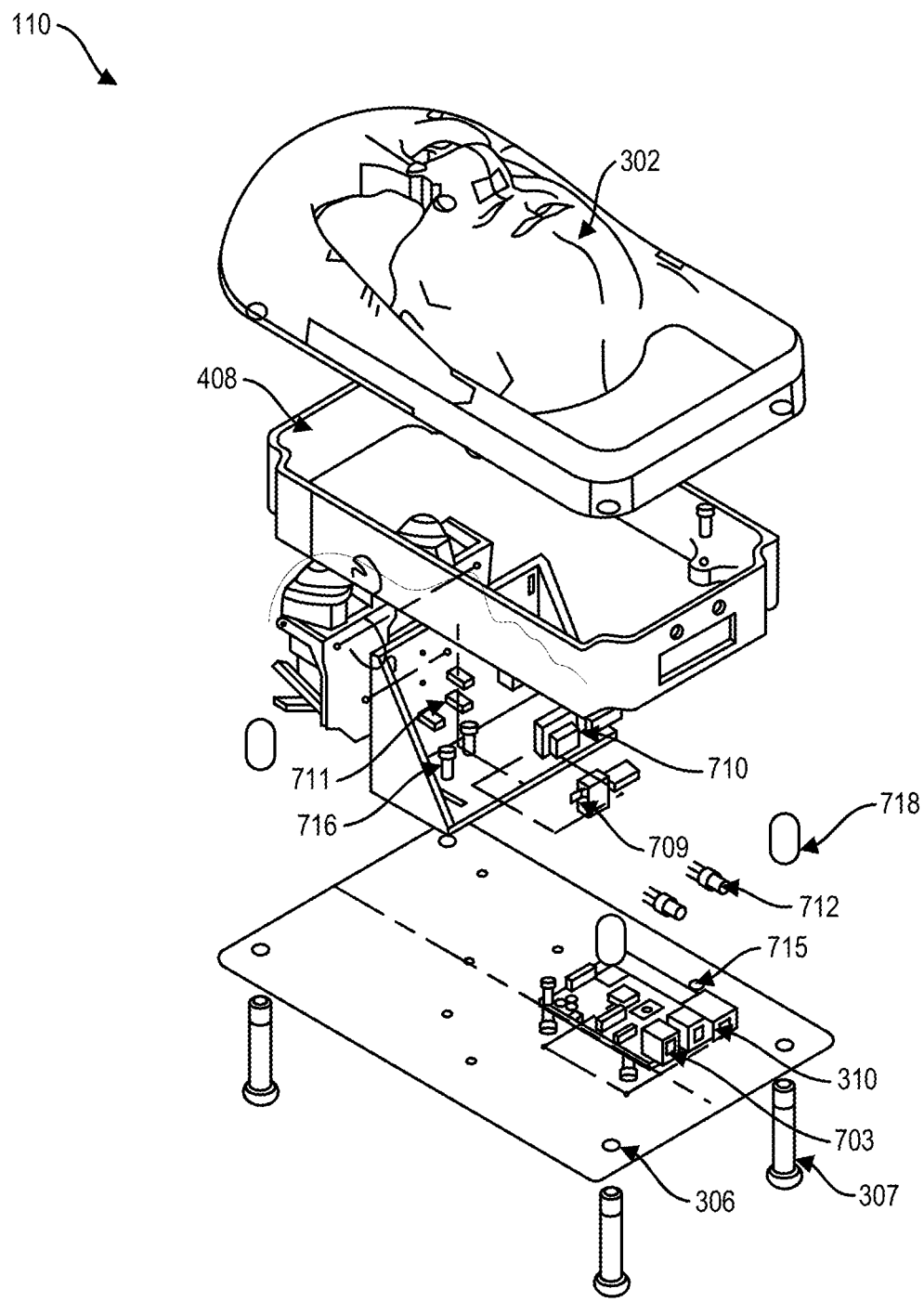
FIG. 7 is an exploded view of the robotics assembly, in accordance with some example implementations.

FIG. 7 is an exploded view of the robotics assembly 110, in accordance with some example implementations. As shown, the robotics assembly 110 includes the base plate 306, the connection pin 307, a first standoff 703, the processor 310, a first bolt 715, a socket 712, a cap 718, a pump 709, an interface board 710, a second standoff 711, a second bolt 716, the shield 408, and the face plate 302. In some aspects, the first standoff 703 may be configured to hold electronics off of the base plate 306. The first bolt 715 may include a 2.5 mm bolt for mounting the processor 310 to the base plate 306. The processor 310 may include a Raspberry Pi or other processor. The socket 712 may include a 12 V socket as an input power socket. The cap 718 may include a rubber cap configured to fit over an 8 mm bolt and may be configured to fit into one or more holes on the bottom of the faceplate 302. The pump 709 may include an aquarium pump configured to provide a vacuum for the eye holder 502 to keep the eye 506 in a desired position. The interface board 710 may provide connections between the processor 310 and servos of the animatronics assembly (e.g., animatronics assembly 600). The second standoff 711 may be configured to mount the interface board 710 to a bracket. The second bolt 716 may include a 4 mm bolt configured to mount the bracket to the base plate 306. The shield 408 may be sized and shaped to at least partially surround a bottom portion of the robotics assembly 110 and may be configured to protect a user from electronics of the robotics assembly. The shield 408 may also provide mounting for a cooling fan and may include one or more holes to allow cables to pass through. The faceplate 302 may include one or more apertures for the robotic eye assembly 304 to be visible. The faceplate 302 may be designed to be the same or similar proportions as a human face to provide realism to the robotics assembly 110. The faceplate 302 may include a tray near a bottom portion configured to collect any liquids. In some aspects, the robotics assembly 110 may include a camera or image capture device (not shown). In some embodiments, the camera or image capture device may be external to the robotics assembly to provide external view of the eye and provide real-time image feedback and/or guidance to a user (e.g., user 202) controlling the robotics assembly 110. The camera or image capture device may also provide feedback regarding an eye position or eye tracking of a fixation point of the eye (e.g., eye 506).

In some aspects, control of telerobotic systems (e.g., systems 100, 250, or the like) may primarily be based on image and video guidance. The involved image acquisition process impacts the portability and transportability of the telerobotic system, while the associated bandwidth demands of the encoded image and video also define to a large extent the telecommunication requirements.

Figure 8A:
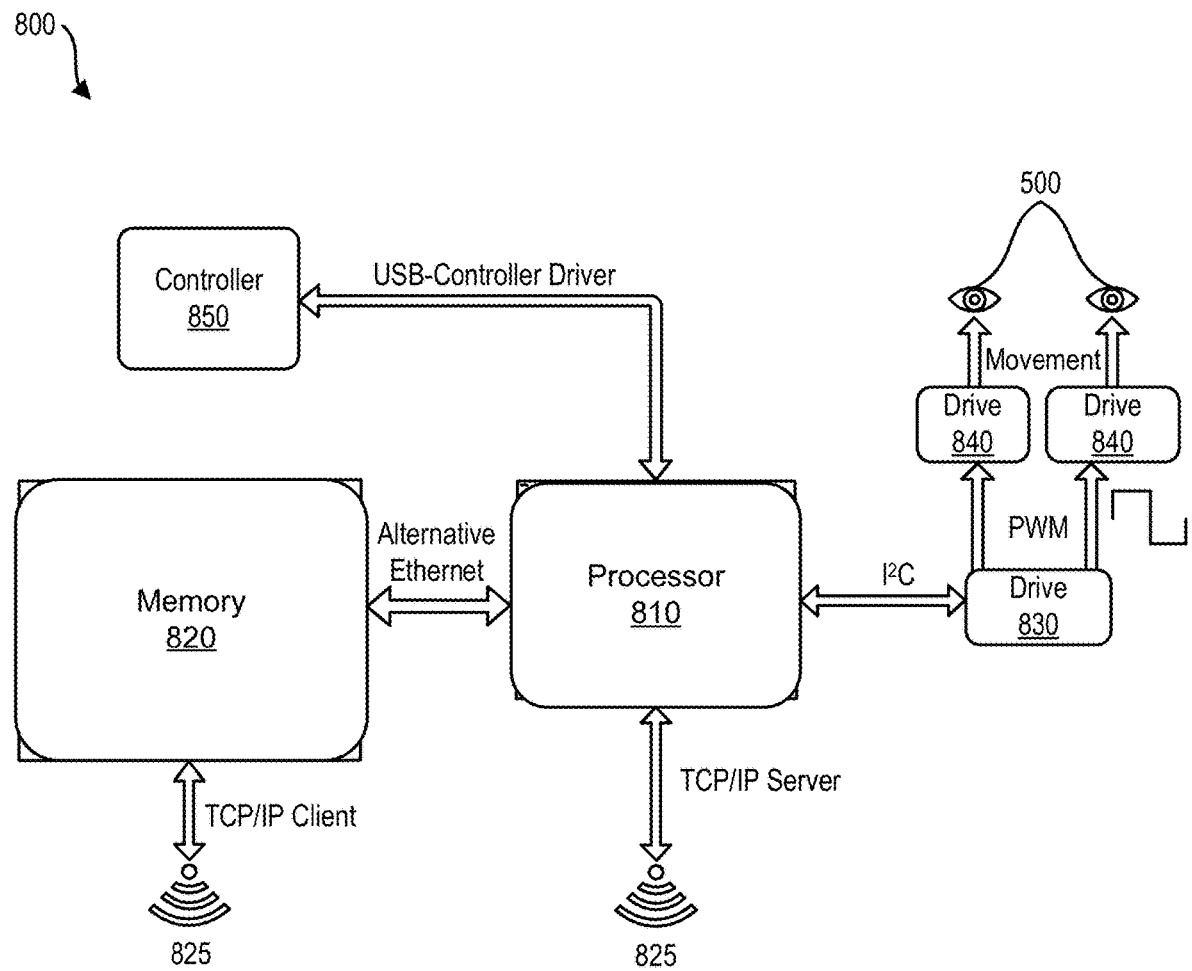
FIG. 8A depicts a block diagram of a system for remote eye surgery training, in accordance with some example implementations.

FIG. 8A depicts a block diagram of a system 800 for remote eye surgery training, in accordance with some example implementations. As shown, the system 800 may include a processor 810, a memory 820, a controller 850, a driver 830, a drive 840, one or more robotic eye assemblies 304, and a wireless connection 825. In some aspects, the processor 810 may include a processor running an operating system (e.g., a Raspberry Pi computer). The memory 820 may store instructions for a graphical user interface application that may cause the processor 810 to perform operations affecting a robotics assembly (e.g., robotics assembly 110) in communication with the system 800. In some aspects, the controller 850 may include a game console controller configured to control eye movement of the robotics assembly. The controller 850 may be coupled to the processor 810 via a USB-controller driver. The processor 810 may be coupled to the driver 830 via an integrated circuit. The driver 830 may be electronically coupled to the drive 840. As shown in the example of FIG. 8, the system 800 includes two drives 840, although more or fewer drives 840 are possible. The drives 840 may include servo drives configured to provide movement to the one or more eye assemblies 304.

Figure 8B:
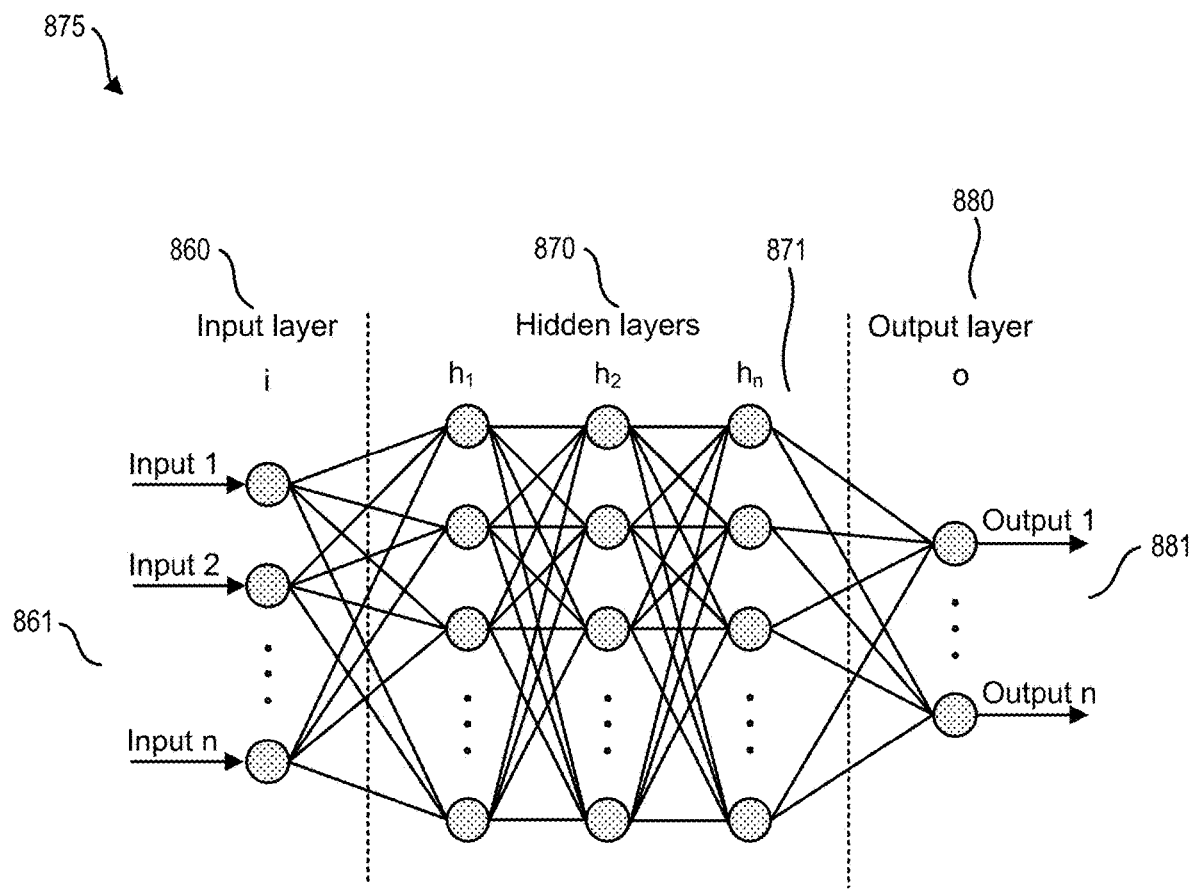
FIG. 8B depicts an example neural network, in accordance with some example implementations.

In some aspects, the system 800 and/or the processor 810 may implement a neural network in order to provide feedback to and from the system. FIG. 8B depicts an example neural network 875, in accordance with some example implementations. As shown, the neural network 875 includes an input layer 860, one or more hidden layers 870, and an output layer 880. Includes one or more input nodes 861. The one or more hidden layers 870 includes one or more hidden nodes 871 and the output layer 880 includes output nodes 881. In some aspects, inputs to the input layer 760 may include digital images, digital videos, mathematical equations, topographical images, wavefront images, optical images, or the like. In some implementations, the one or more hidden layers 870 can perform calculations, utilize physics tools, include modulators, algorithms, digital code, trigger functions, perform catalyst and modular transfer functions, or the like. Outputs to the output layer 880 may include physical indicators, mathematical indicators optical indicators, motion indicators, or the like.

Figure 9A:
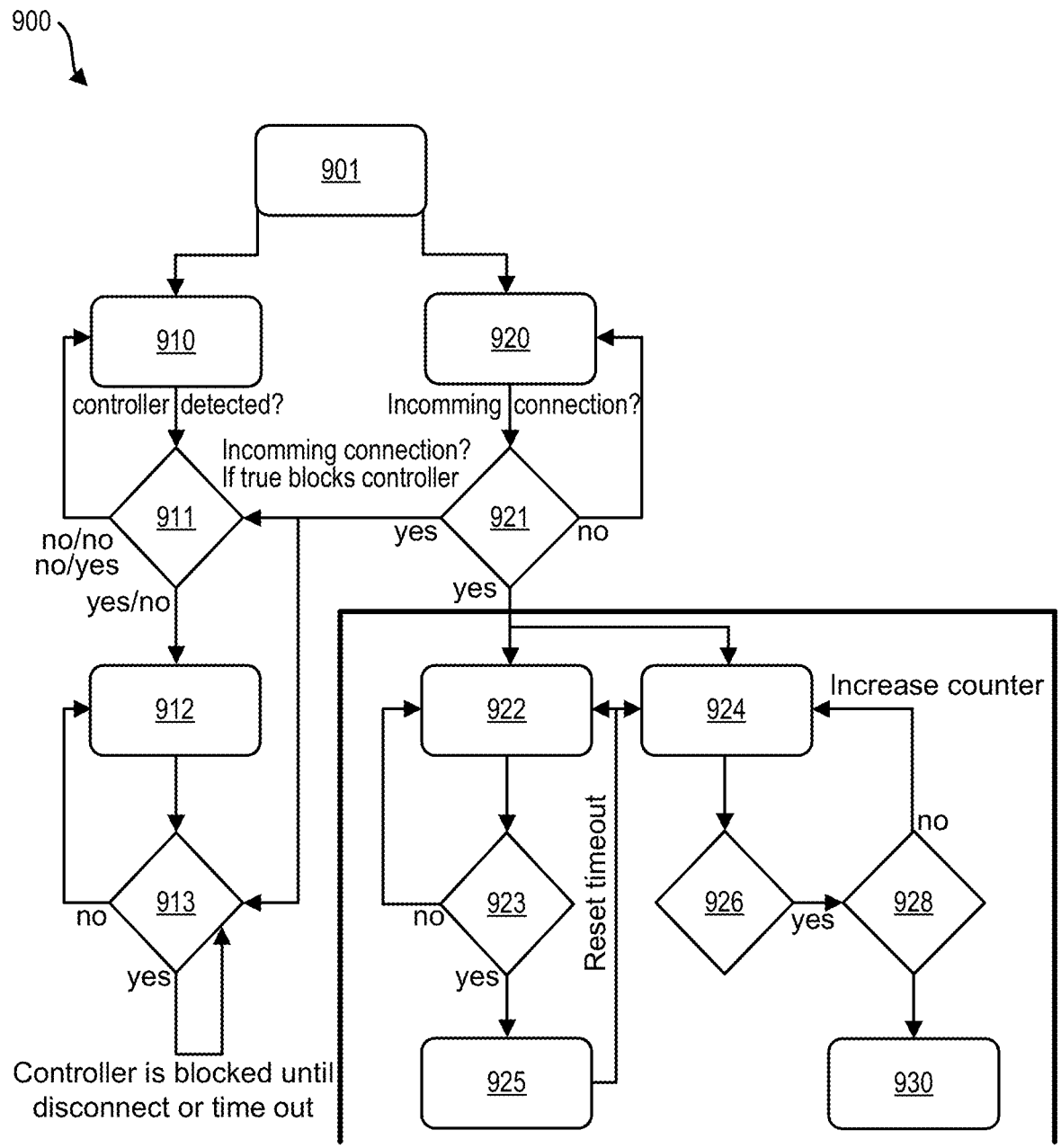
FIG. 9A depicts a flowchart of an example program execution, in accordance with some example implementations.

FIG. 9A depicts a flowchart 900 of an example program execution for controlling robotic operations in a robotic system (e.g., system 100), in accordance with some example implementations. In some aspects, the flowchart 900 may be executed by the processor 310, 810, the neural network 875, or the like.

Figure 9B:
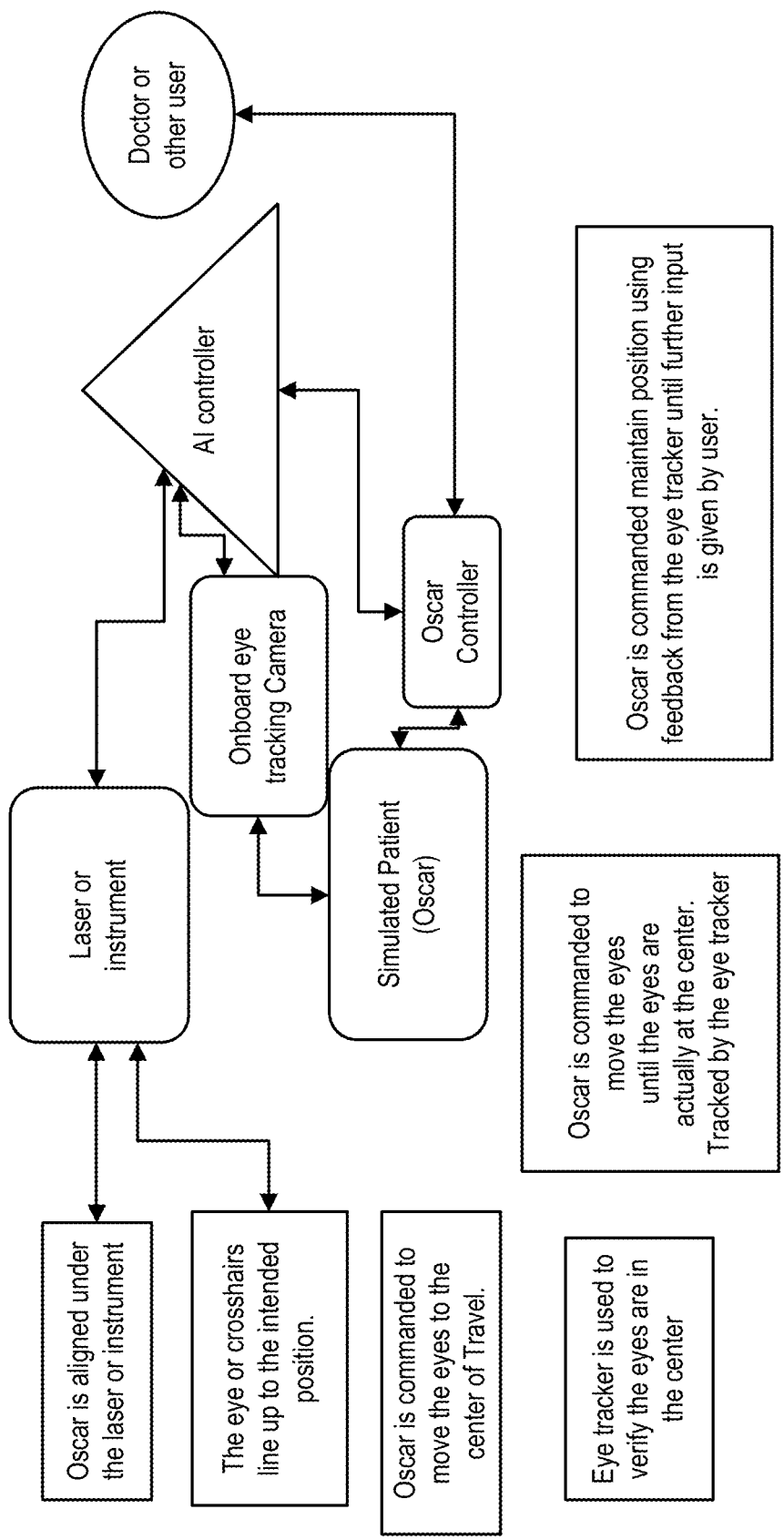
FIG. 9B depicts an example workflow and automatic feedback loops, including eye tracking feature, in accordance with some example implementations.

FIG. 9B depicts an example workflow and automatic feedback loops 950, in accordance with some example implementations. As shown, the workflow and feedback loops 950 show example interactions between a laser or instrument, an artificial intelligence controller, a simulated patient (e.g., animal or human, robotics assembly 110), a doctor or other user, and an onboard eye tracking camera.

In some aspects, a robotic assembly (e.g., assembly 110) may operate in an autonomous, semiautonomous, telerobotic state. In telerobotic systems (e.g., see FIG. 2C), a remote manipulator (e.g., controller 150) may be controlled from an operator's (e.g., a user's 202) site by sending position commands while receiving visual and other sensory feedback information (e.g., from a camera internal or external to the robotics assembly 110). Local and remote systems may be referred to as "master" and "slave" systems, respectively, and the overall system (e.g., system 250) may be referred to as a "master-slave system". The remote manipulator may be programmed to track the controls of the operator (e.g., user 202). In some aspects, the robotics assembly 110 may include one or more sensors that may provide positional triggers and/or feedback that indicate whether an eye of the assembly 110 (e.g., eye 506) in a desired position, such as via a visual camera. Image processing may occur during a training or procedure. The image processing may include both digital captured images and live video acquisition. Synchronization may occur between the two or more cameras. Synchronization may involve a bidirectional navigation system (BNS) which implements a feedback loop control to confirm the synchronization and data acquisition. This may be controlled by an artificial intelligence system (e.g., neural network 875, the processor 810, etc.) and may be automated, corresponding to the system operating in an autonomous state. In a semiautonomous state, the processor 810 may perform all the functions and controls for the robotics assembly 110 but may also receive user inputs (e.g., from a user 202).

The program execution may begin at step 901 which may start the script for program execution. At step 910, the processor may execute a controller loop to determine if a controller is connected to the remote eye surgery training system. At step 911, the processor may determine whether a controller (e.g., controller 150) is detected. If no controller is detected, the program may return to step 910. If a controller is detected, the program may proceed to step 912. At step 912, the detected controller may be configured to control a robotics assembly (e.g., the robotics assembly 110). After the detected controller gains control of the robotics assembly, at step 913 the processor may check to determine if there is an incoming connection (e.g., the wireless connection 825) that may override the detected controller.

In some aspects, when the processor executes the controller loop at step 910, the processor may also keep execute a parallel wireless connection loop at step 920. In some aspects, the wireless connection loop may include adaptive feedback to correct any missed signals, delays and communication, or the like. At step 921, the processor determines if there is an incoming wireless connection. If a graphical user interface (GUI) connects via a matching IP address and port, the controller execution may be blocked. The robotics assembly may be controlled via the remote GUI. This may happen until the GUI is closed or the connection is lost. If the there is an incoming wireless connection (e.g., the wireless connection 825, a wireless pairing, etc.) the program proceeds to step 922 where the processor may receive messages from a client device (e.g., laptop, tablet, computer, or the like). In some aspects, the messages may include commands to move or otherwise control the robotics assembly. If the messages are received, then at step 923, the processor (e.g., via a decision engine) may check to determine if the messages are valid. If not, the program may return to step 922. If the messages are valid, then at step 925, the processor may execute the command. After an incoming wireless connection is detected at step 920, at step 924, the processor may start a timeout counter to determine if connection has been lost. At step 926, the processor may determine if a timeout value has been satisfied, indicating a timeout. If yes, then at step 928 processor may determine if a timeout counter is equal to or less than a timeout counter threshold (e.g., ten (10)). If not, the processor may increase the counter and return to step 924. If the timeout counter has satisfied the threshold, then the program may proceed to step 930 and disconnect the robotics assembly from the client device and release any wireless connection (e.g., the wireless connection 825, wireless pairing, or the like).

Figure 10A:
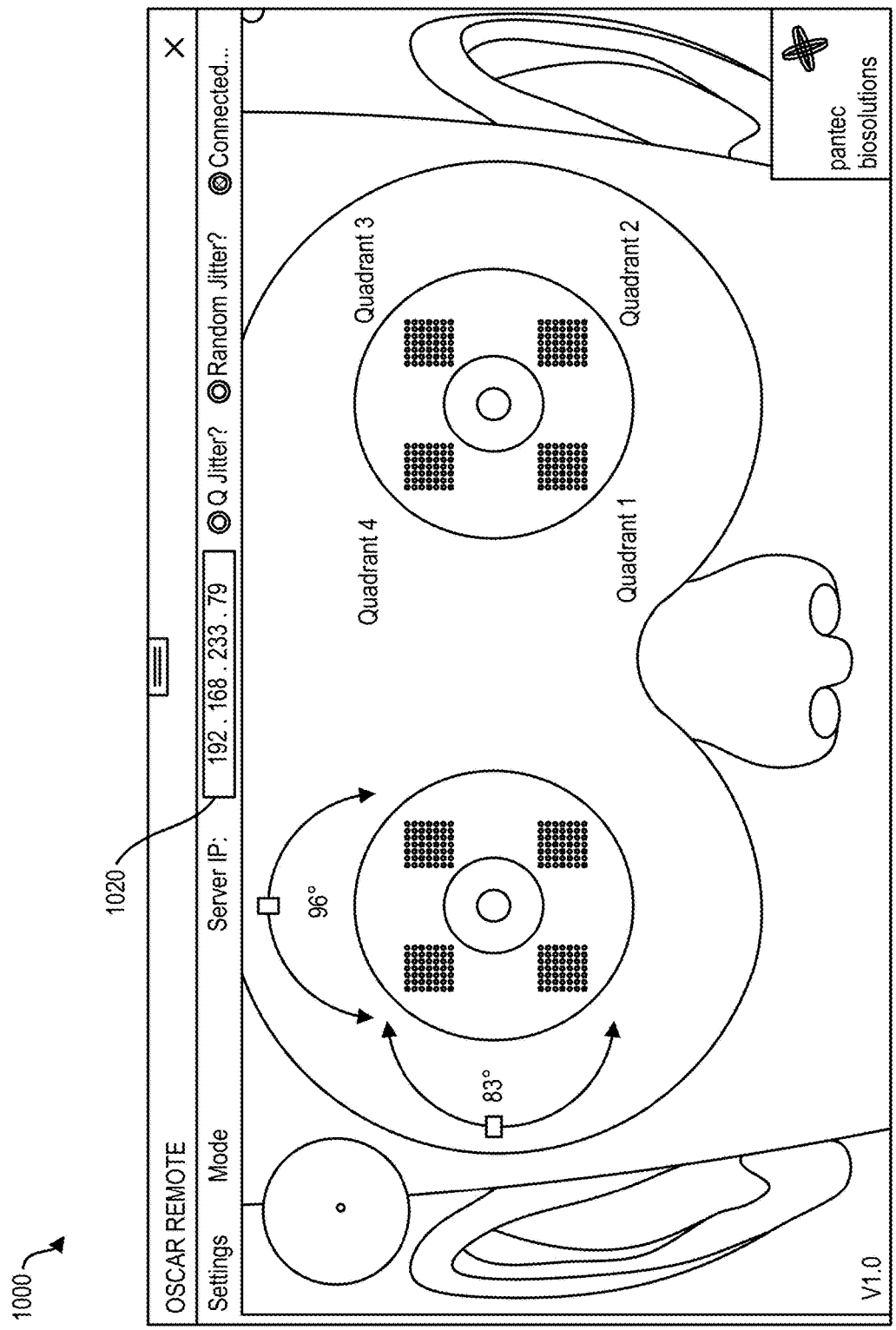
FIGS. 10A-10C depict example graphical user interfaces for interacting with the remote eye surgery training system, in accordance with some example implementations.
Figure 10B:
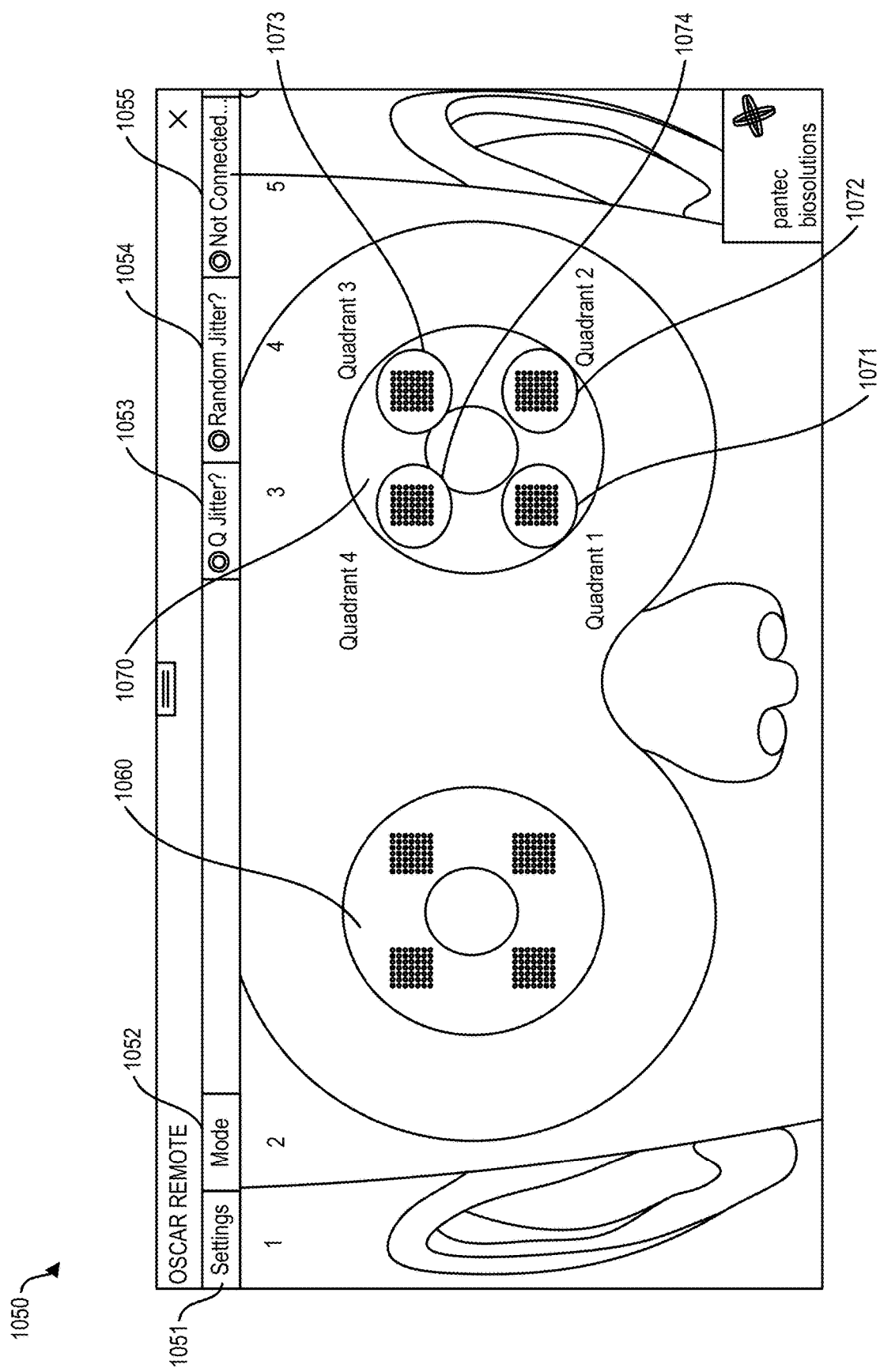
Figure 10C:
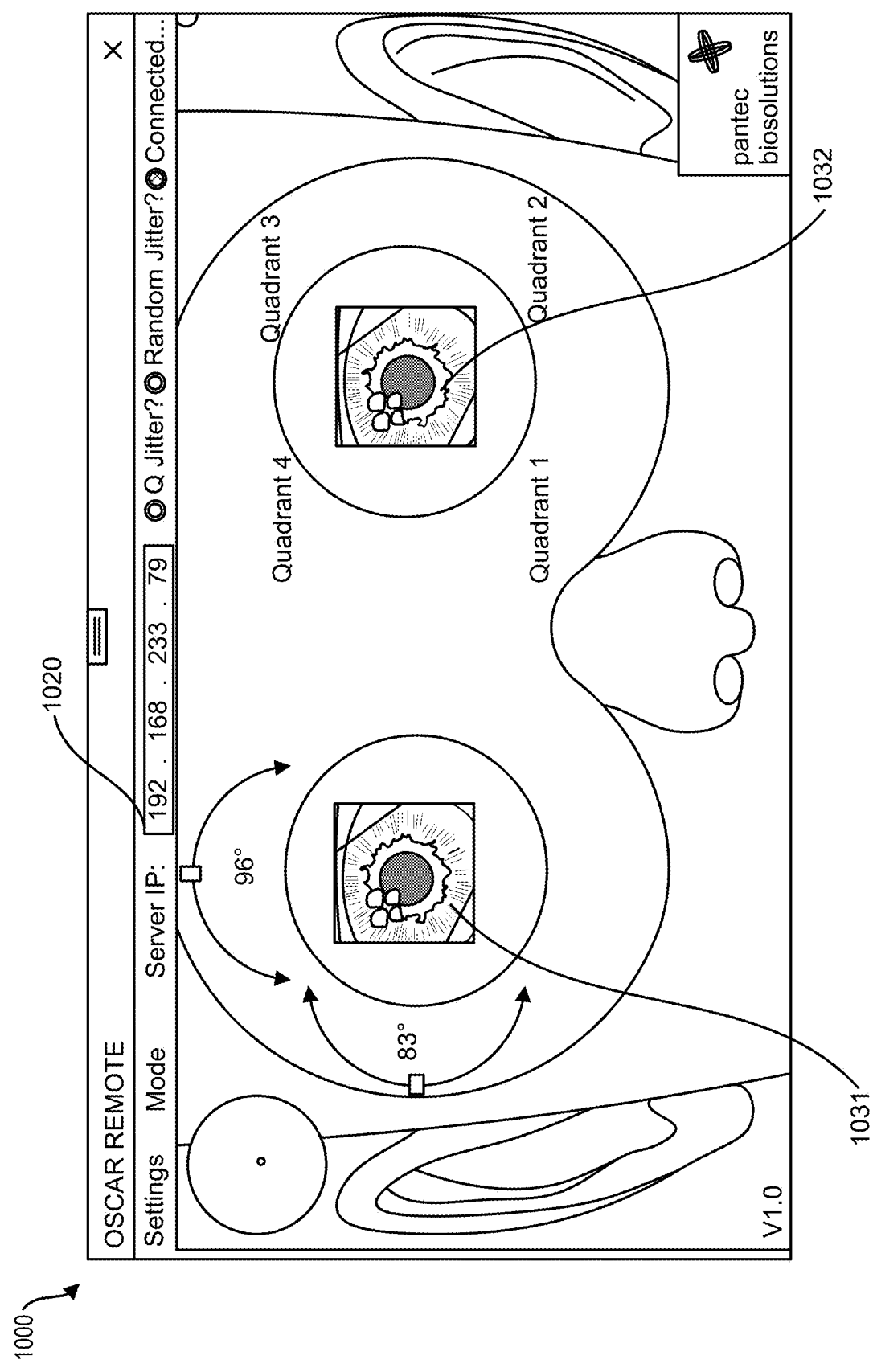

In some aspects, in order to control the robotics assembly 110, a graphical user interface (GUI) may be designed to improve user experience and control over the robotics assembly 110. FIGS. 10A-10C depict example graphical user interfaces for interacting with the remote eye surgery training system, in accordance with some example implementations. FIG. 10A is an example screenshot of a GUI 1000. As shown, the GUI 1000 includes an IP address field 1020. In some aspects, this field may be automatically populated with an IP address of a client device. In some implementations, a user may input an IP address to connect to the robotics assembly 110. In some aspects, if the field 1020 is populated with a valid IP address, this indicates that the robotics assembly 110 has established a wireless connection and may be controlled by the GUI 1000.

FIG. 10B depicts a screenshot 1050 of the GUI 1000 after startup of the GUI application. As shown, certain features of the GUI 1000 are highlighted in the top portion of the screen. For example, the screenshot 1050 includes a settings feature 1051, a mode feature 1052, a ginger feature 1053, a random jitter feature 1054, and a not connected feature 1055. In some embodiments, the settings feature 1051 may open a menu to adjust any settings of the GUI 1000. For example, the settings menu may include a connect element configured to connect to a target system (e.g., a client system 205). The settings menu may further include a disconnect element configured to disconnect from the target. The settings menu may further include an interval for quadrant jitter functionality configured to adjust jitter settings for one or more quadrants of an eye portion (e.g., eye portion 1060 and/or 1070). The settings menu may further include a profile element configured to open a profile sub-window. While certain settings are described herein more or fewer settings elements are possible. In some aspects, the mode feature 1052 may be selected to open a mode menu to adjust in operation mode of the GUI 1000. For example, the mode menu may include a random jitter mode which may start a random movement loop of one or more eyes. The mode menu may include a start profile element that may open a file dialog in which a user may select a file with a drive profile. While certain settings and modes are described herein, additional or fewer modes and settings are also possible.

As further shown in FIG. 10B, the GUI 1000 further includes a right eye portion 1060 and a left eye portion 1070. In some aspects, one or more of the eye portions 1060 and 1070 may include four quadrants. In the example of FIG. 10B, the left eye portion 1070 includes a first quadrant 1071, a second quadrant 1072, a third quadrant 1073, and a fourth quadrant 1074. Further includes anatomical zones, central, superior, nasal, inferior, and temporal. In some implementations, the eye quadrants may allow a doctor or medical professional to highlight, visualize, diagnose & treat certain areas of an eye anatomy not possible with static methods facilitating a realistic live surgical or diagnostic experience with a cadaver eye ex vivo.

Figure 10D:
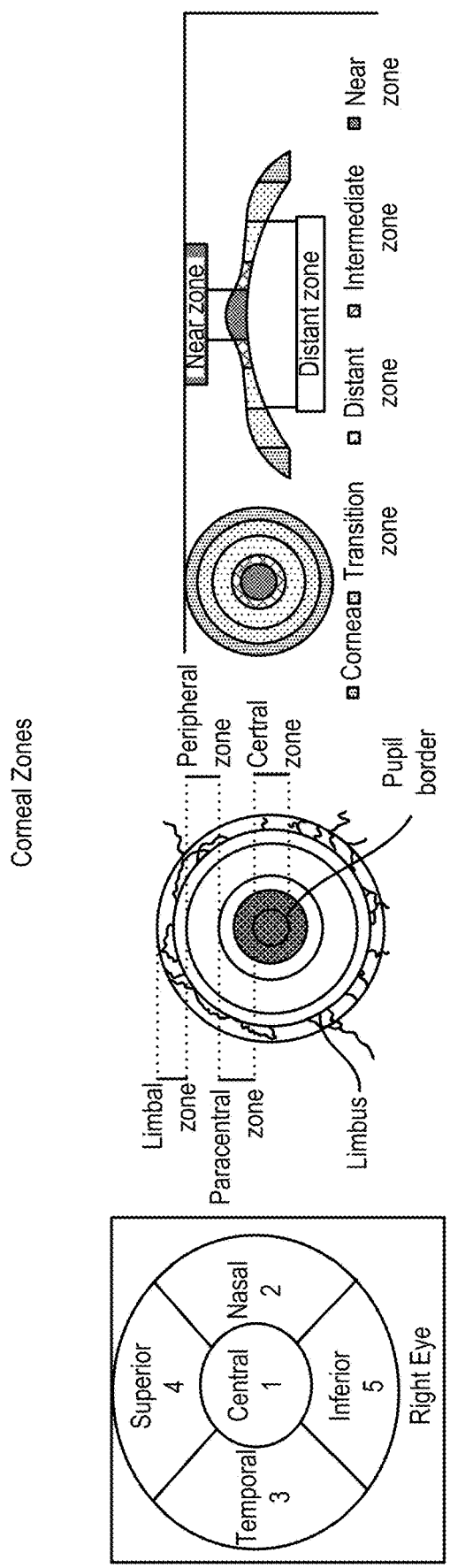
FIGS. 10D and 10E depicts various optical zones, in accordance with some example implementations.
Figure 10E:
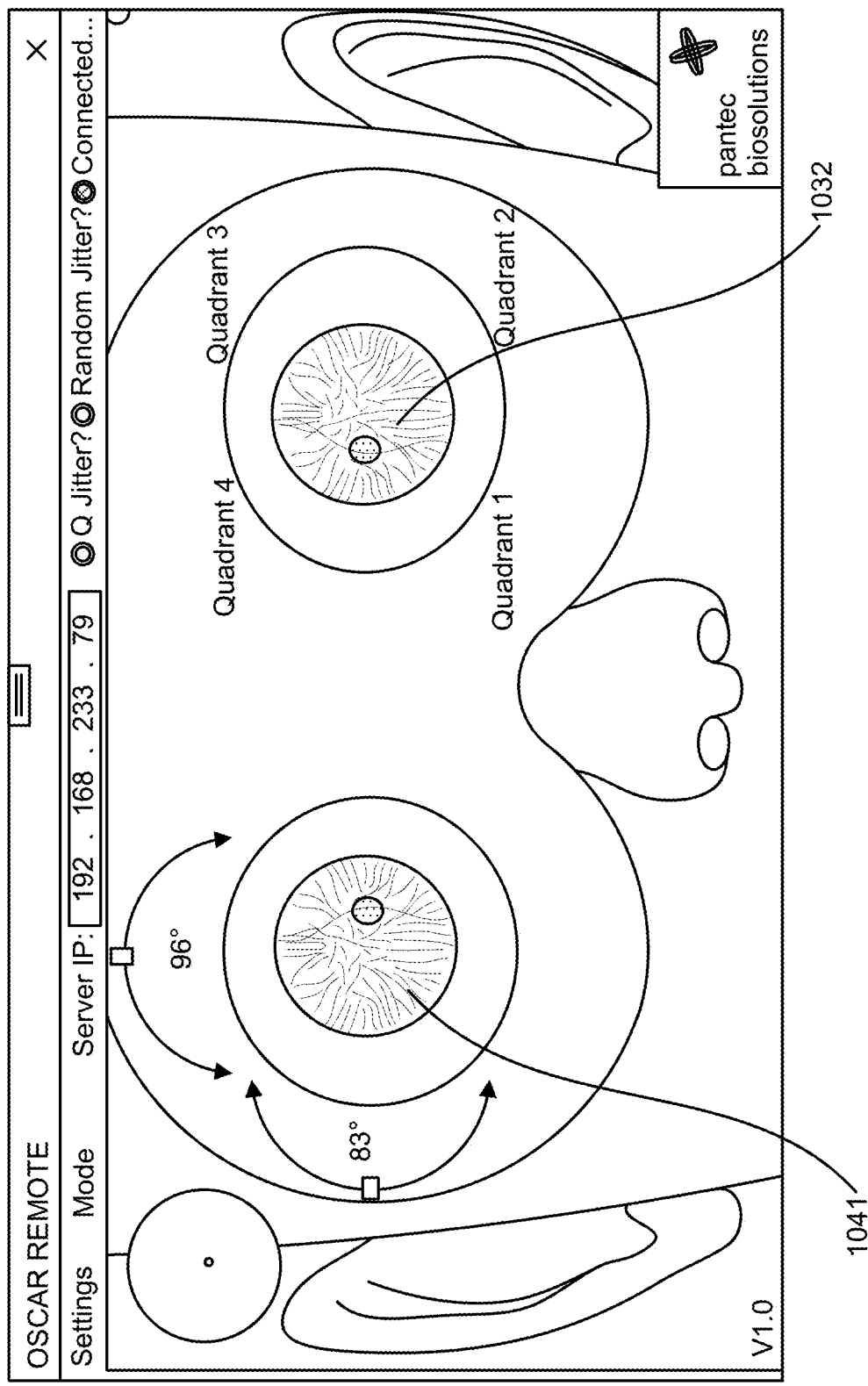

As further shown in FIG. 10C, the GUI 1000 further includes a right eye cornea 1031 and a left eye cornea 1032. In some aspects, may include one or more zones of the cornea, limbal, central, paracentral, peripheral, or the like. For example, FIGS. 10D and 10E, depicts various optical zones such as cornea, transition zone, distance zone, intermediate zone, and near zone. As further shown, the optical zones may include anatomical zones: central (1), superior (4), nasal (2), inferior (5), and temporal (3). In some implementations, the eye zones may allow a doctor or medical professional to highlight, visualize, diagnose & treat certain areas of an eye anatomy not possible with static methods facilitating a realistic live surgical or diagnostic experience with a cadaver eye ex vivo.

As further shown in FIG. 10E1, the GUI 1000 further includes a right eye scleral quadrants and a left eye scleral quadrants). In some aspects, the quadrants may include one or more quadrants including Superior Nasla, Inferior Nasal, Superior Temporal, Inferpior temperal or the entire 360 circumference. As further shown, the optical zones may include anatomical zones: central (1), superior (4), nasal (2), inferior (5), and temporal (3). In some implementations, the eye zones may allow a doctor or medical professional to highlight, visualize, diagnose & treat certain areas of an eye anatomy not possible with static methods facilitating a realistic live surgical or diagnostic experience with a cadaver eye ex vivo.

Figure 10F:
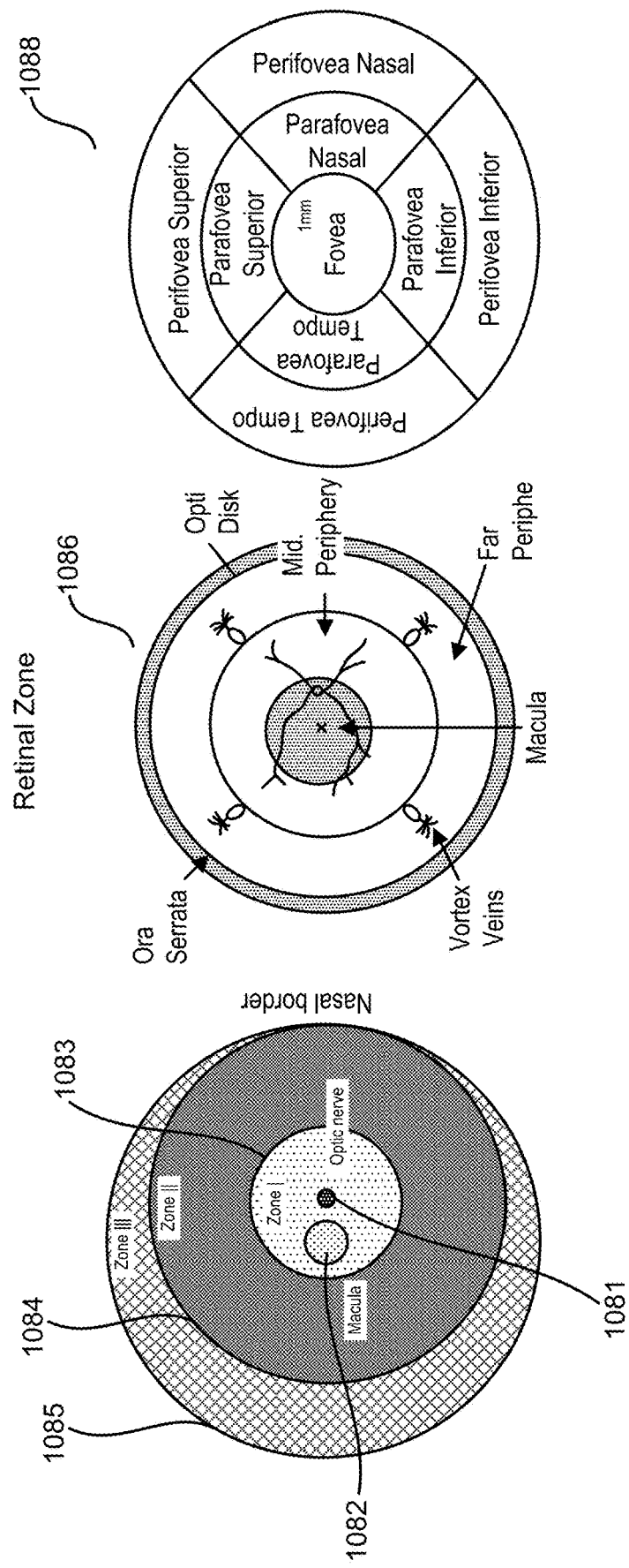
FIG. 10F depicts one or more example retinal zones, in accordance with some example implementations.

As further shown in FIG. 10E, the GUI 1000 may further include a right eye retina 1041 and a left eye retina 1042. In some aspects, a retina may include one or more zones. FIG. 10F depicts one or more example retinal zones. As shown:

Zone I (1083) is the small circle of the retina around the optic nerve 1081. The radius of the circle may be twice the distance from the macula 1082 to the center of the optic nerve 1081

Zone II (1084) is the ring-shaped section of the retina surrounding zone I, which extends to the ora serrata on the nasal side Zone III (1085) is a crescent-shaped area of temporal retina.

FIG. 10F further includes retinal landmarks 1086 including: Central (Fovea, macula optic disc), mid periphery (vortex veins), far periphery (ora serrata) In some implementations, the eye zones may allow a doctor or medical professional to highlight certain areas of an eye anatomy and facilitate a realistic live surgical or diagnostic experience with a cadaver eye ex vivo.

FIG. 10F further includes anatomical zones 1088 including: Fovea, perifoveal superior, perifoveal nasal, perifoveal inferior, perifoveal temporal; parafoveal superior, parafoveal nasal, parafoveal inferior, parafoveal temporal.

In some implementations, the eye zones may allow a doctor or medical professional to highlight, visualize, diagnose & treat certain areas of an eye anatomy not possible with static methods facilitating a realistic live surgical or diagnostic experience with a cadaver eye ex vivo.

Figure 10G:
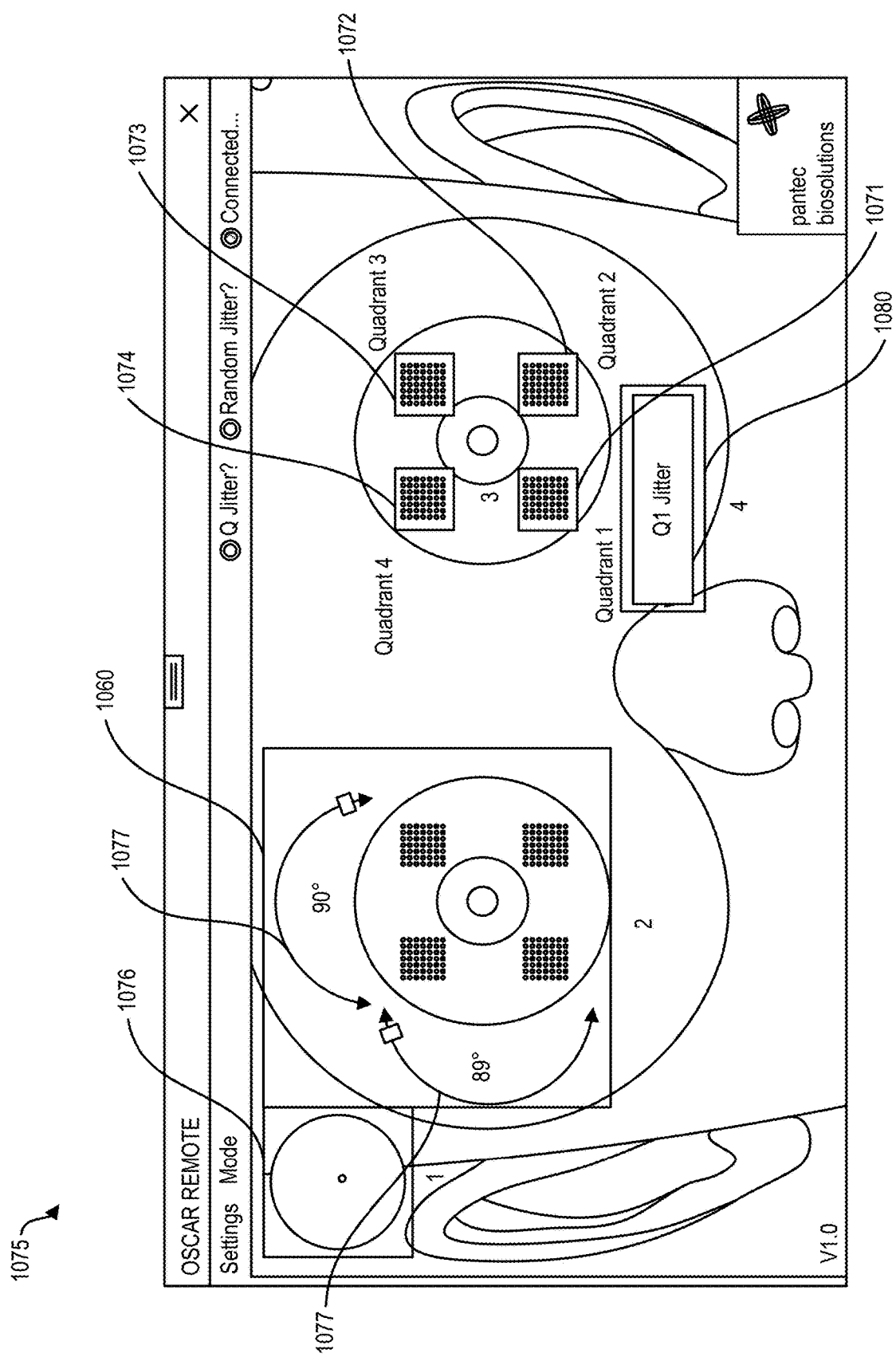
FIG. 10G depicts an example screenshot of a GUI.

FIG. 10G depicts an example screenshot 1075 of the GUI 1000 after startup of the GUI application. As shown, the GUI 1000 includes a virtual joystick area 1076. The virtual joystick area 1076 may show the movement region of the eyes. A user may click somewhere in this region and the eyes of the robotic assembly 110 may move to that position. The GUI 1000 further includes a right eye portion 1060 that includes curved sliders 1077. The curve sliders 1077 may be configured to provide fine adjustments via a mouse selection to change the values of the sliders and start a movement of the eye. The GUI 1000 further includes the four quadrants 1071, 1072, 1073, and 1074. A user may click on a portion of a particular quadrant and the corresponding eye may move to the assigned quadrant. As further shown in the example of FIG. 10C, if a user performs a right click on one or more of the quadrants, a quadrant jitter button 1080 may appear to start a quadrant jitter mode.

Figure 11A:
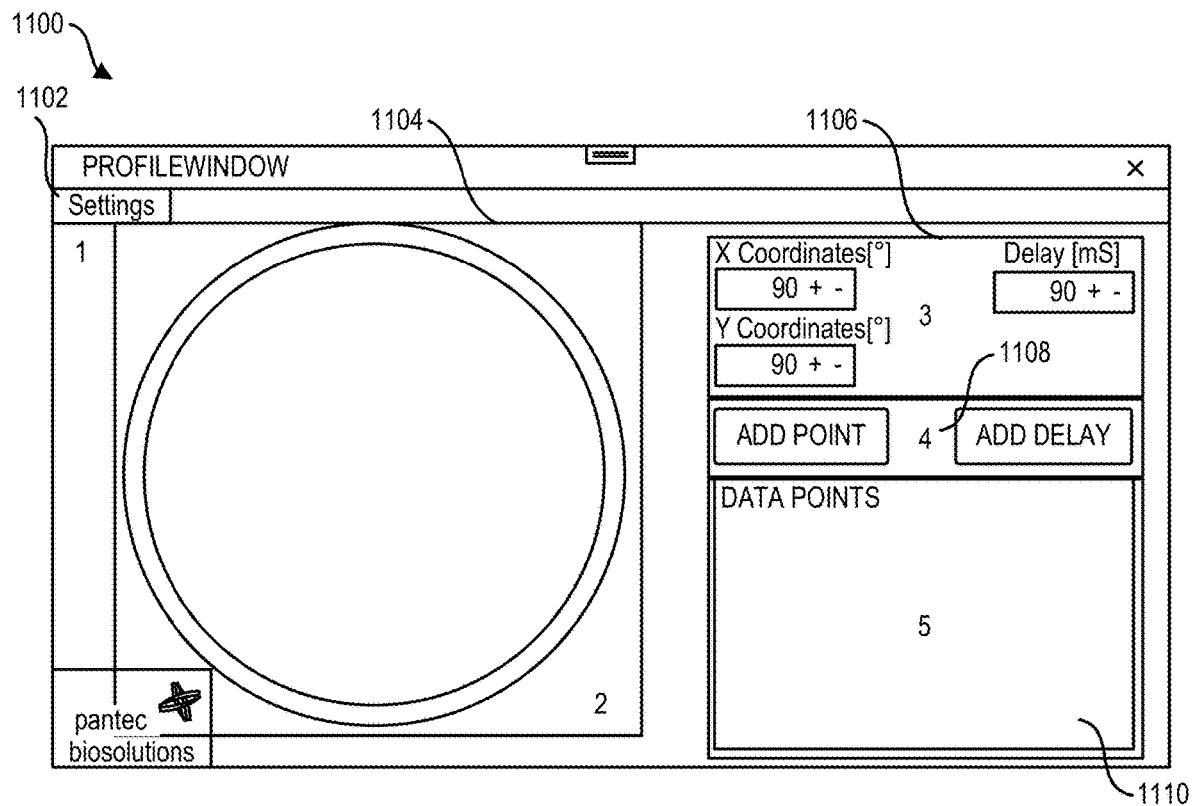
FIGS. 11A-11B depict example profile windows of a graphical user interface, in accordance with some example implementations.
Figure 11B:
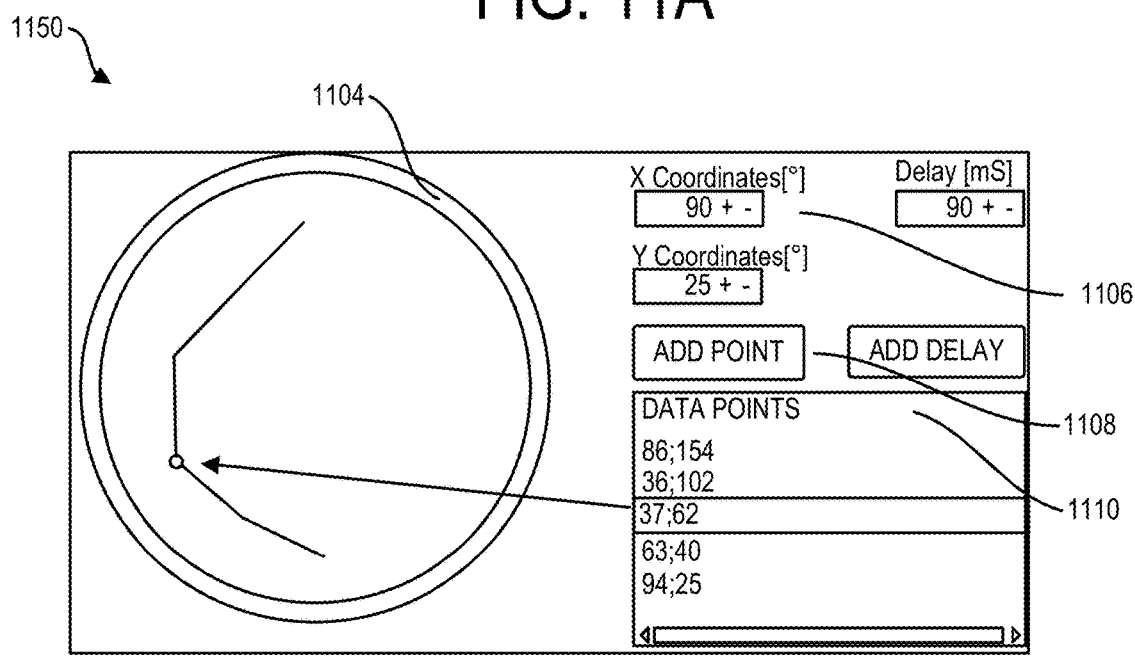

FIGS. 11A-11B depict example profile windows of a graphical user interface, in accordance with some example implementations. For example, after selecting a profile element from the settings menu, a new window may appear. FIG. 11A depicts an example profile window 1100. As shown, the profile window 1100 may include a settings menu 1102, a move area 1104, a numeric field(s) area 1106, a button(s) area 1108, and data point(s) area 1110. In some aspects, the settings menu 1102 may include an add delays element which may allow a user to add multiple delays to the current driving profile. For example, if a user draws a driving profile with approximately 100 points the user may need to give the engine time for movement. With the add delay function, the user can add a current set delay in the delay control between every point in the list. The settings menu 1102 may further include a save profile element configured to let the user save the current driving profile. The settings menu 1102 may further include a load profile element which may allow a user to open a file dialog to let the user load a saved driving profile. The settings menu 1102 may further include a clear element configured to clear the current set up. The settings menu may further include a freestyle element configured to allow the user to draw the driving route with a mouse or other input device.

In some aspects, in connection with the profile window of the graphical user interface, a bidirectional navigation system (BNS) may implement a feedback loop control to confirm the synchronization and data acquisition. The BNS may also confirm the robotics assembly 110 and/or the eye 506 is moving in accordance with the controls on the graphical user interface. The BNS may include one or more cameras or image capture devices to confirm a position of the robotics assembly 110 and/or the eye 506. The one or more cameras or image capture devices may also provide guidance to the medical professional or user controlling the robotics assembly 110 to confirm the accuracy and veracity of the controls.

In some implementations, the move area 1104 may be configured to allow a user to select a target point via a selection using a mouse. After the selection, X and Y coordinates may change to the selected target point. If the freestyle mode option has been selected, a user may freely draw a driving route. The numeric field(s) area 1106 may include a field for X coordinates, Y coordinates, delay (milliseconds), or the like. While certain fields are shown in the example of FIG. 11A, other fields are possible. In many cases, a user may only change the value of the delay field. The button(s) area 1108 may include buttons to add a data point or add a delay. In some aspects, after pressing one of these buttons, the value may be transferred to the list box (e.g., the data point area 1110). The data point area 1110 may include a listbox of data points. All assigned positions and delays may appear in this list. It may be possible to delete data points in the list box with a right-click on one or more elements. With the data in this list of the data point area 1110, an XML file may be created later.

FIG. 11B depicts an example profile window 1150. As shown, the profile window 1150 includes the move area 1104, the numeric field(s) area 1106, the button(s) area 1108, and the data point(s) area 1110. As further shown, a data point (e.g., 37; 62) has been selected in the data point(s) area 1110 and is highlighted in the move area 1104.

Figure 12:
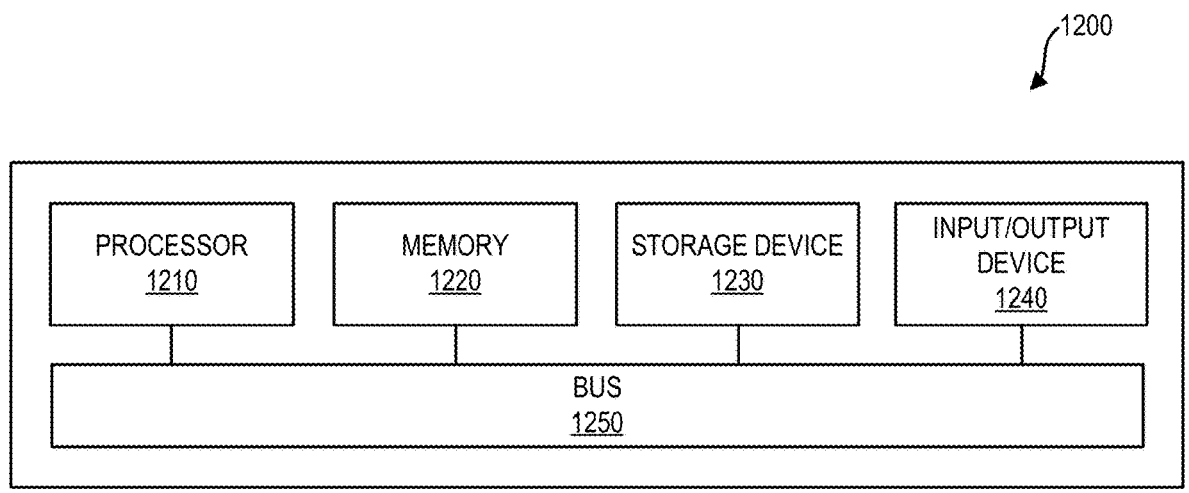
FIG. 12 depicts a block diagram of an example computing apparatus, in accordance with some example implementations.

FIG. 12 illustrates an example computing apparatus 1200 which may be used to implement one or more of the described devices and/or components, in accordance with some example implementations. For example, at least a portion of the computing apparatus 1200 may be used to implement at least a portion of the client device 205, the server 225, the processor 310, or the like. Computing apparatus 1200 may perform one or more of the processes described herein.

As illustrated, computing apparatus 1200 may include one or more processors such as processor 1210 to execute instructions that may implement operations consistent with those described herein. Apparatus 1200 may include memory 1220 to store executable instructions and/or information. Memory 1220 may include solid-state memory, solid-state disk drives, magnetic disk drives, or any other information storage device. In some aspects, the memory 1220 may provide storage for at least a portion of a database. Apparatus 1200 may include input/output devices 1240 to a wired network or a wireless network (e.g., wireless connection 825). Wireless networks may include radio antenna, Wi-Fi, WiMax, WAN, WAP Bluetooth, satellite, and cellular networks (2G/3G/4G/5G), and/or any other wireless network. In order to effectuate wireless communications, the input/output devices 1240, for example, may utilize one or more antennas.

Apparatus 1200 may include one or more user interfaces, such as graphical user interface 1100. The user interface can include hardware, software, or firmware interfaces, such as a keyboard, mouse, or other interface, some of which may include a touchscreen integrated with a display. The display may be used to display information such as promotional offers or current inventory, provide prompts to a user, receive user input, and/or the like. In various implementations, the user interface can include one or more peripheral devices and/or the user interface may be configured to communicate with these peripheral devices.

In some aspects, the user interface may include one or more of the sensors described herein and/or may include an interface to one or more of the sensors described herein. The operation of these sensors may be controlled at least in part by a sensor module. The apparatus 1200 may also comprise and input and output filter, which can filter information received from the sensors or other user interfaces, received and/or transmitted by the network interface, and/or the like. For example, signals detected through sensors can be passed through a filter for proper signal conditioning, and the filtered data may then be passed to the processor 1210 for validation and processing (e.g., before transmitting results or an indication via the input/output devices 1240). In some aspects, the filter may be part of the adaptive feedback loop described herein. The apparatus 1200 may be powered through the use of one or more power sources. As illustrated, one or more of the components of the apparatus 1200 may communicate and/or receive power through a system bus 1250.

Figure 13:
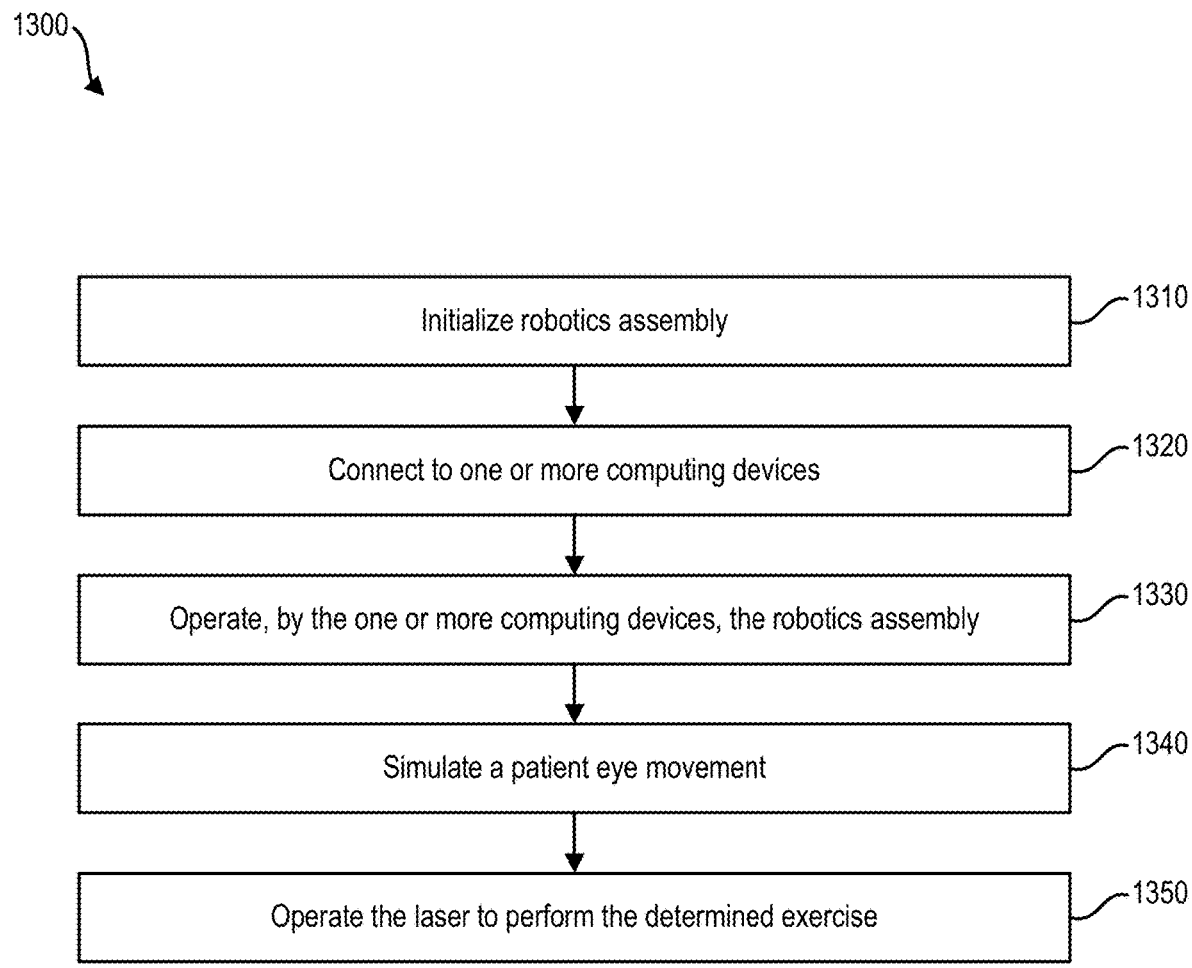
FIG. 13 depicts an example of a method for remote eye surgery training, in accordance with some example implementations.

FIG. 13 illustrates a flowchart of a method for remote eye surgery training, in accordance with some example implementations. In various implementations, the method 1300 (or at least a portion thereof) may be performed by one or more of the robotics assembly 110, the client device 205, the server 225, the processor 310, the computing apparatus 1200, other related apparatuses, and/or some portion thereof.

Method 1300 can start at operational block 1310 where the apparatus 1200, for example, can initialize the robotics assembly 110. In some aspects, initializing the robotics assembly 110 can include initializing the robotics assembly at a location where a laser for eye surgery is disposed. Initializing the robotics assembly 110 can also include installing a glass eye, a wooden eye, a cadaver eye, or the like (e.g., the eye 506) into the robotics assembly 110 (e.g., via the robotic eye assembly 304). Initializing the robotics assembly 110 may also include using an eye tracking system to track a position of the eye 506 and confirm the position is in a desired location. For example, a doctor, a moderator, technician or other medical professional may direct a human or animal or simulated human or animal where to look for a given training exercise. A user (e.g., user 202) may command the robotics assembly 110 to move one or more eyes 506 to a target position. The eye tracking system may verify that the one or more eyes are in the target position. If the eye tracking system determines the one or more eyes 506 are not in the target position, the user 202 may make adjustments or the robotics assembly 110 may automatically adjust the eye position of the one or more eyes 506 (e.g., in the autonomous state using AI, the neural network 875, or the like) until the determined eye position is within a threshold of the target position. The eye tracking artificial intelligence or neural network 875 may be trained to be used for any ex vivo animal or human study. In some aspects, the eye tracking artificial intelligence or neural network 875 may be trained to find or look a specific target. For example, a camera laser pointer or mirror inside the eye holder 502 that can detect or follow an external point source or spot on a screen. The eye tracking feedback system can direct the eye and control the spot until the one or more eyes 506 can track any target presented. The eye tracker may follow the eye and the camera (or mirror) tracks where the eyes 506 are looking and may correct until they match. This system allows for fine, dynamic, real-time adjustments of the eye direction of the one or more eyes 506.

Figure 14A:
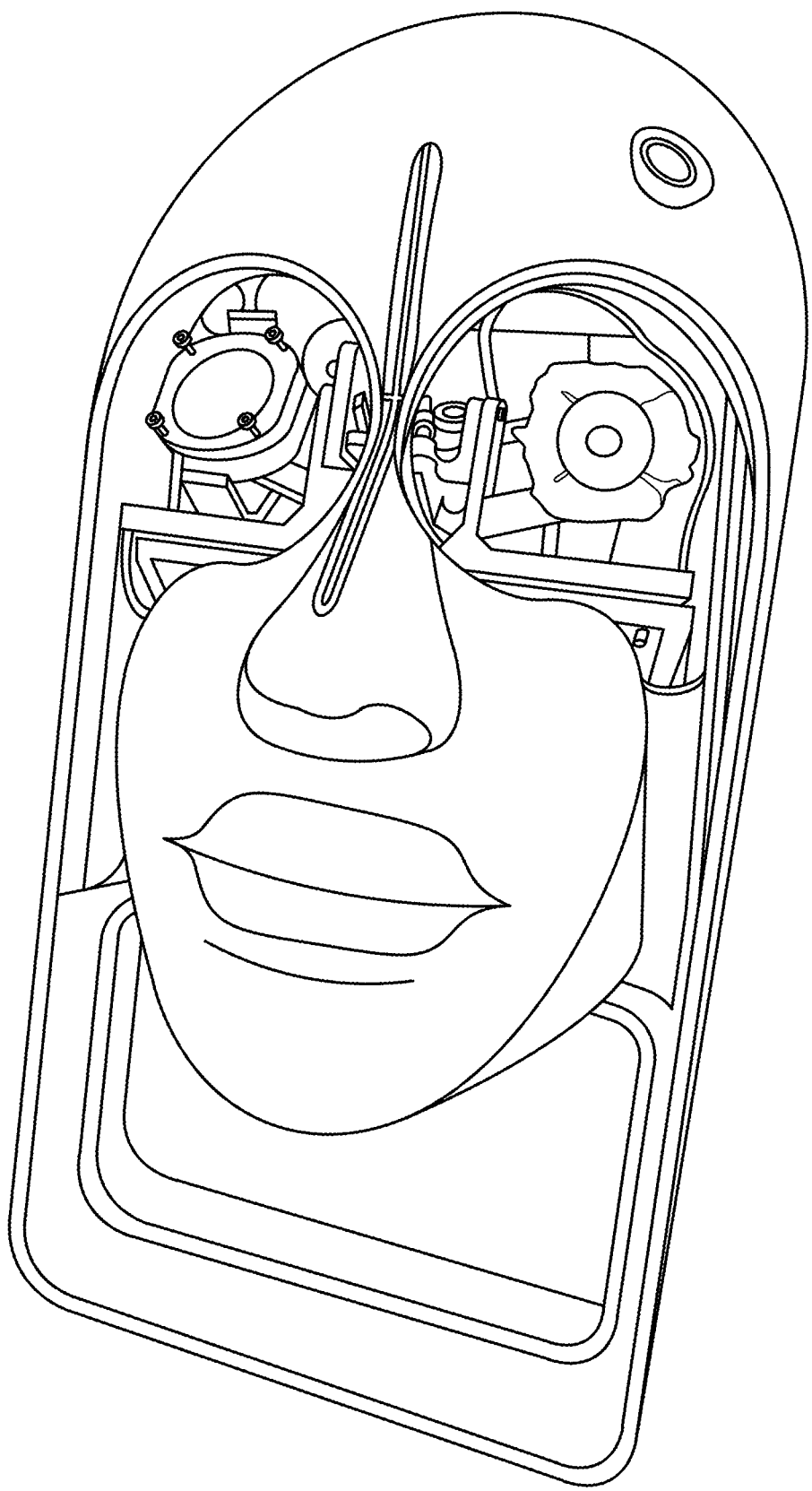
FIGS. 14A and 14B depicts an example robotics assembly and eye tracker, in accordance with some example implementations.
Figure 14B:
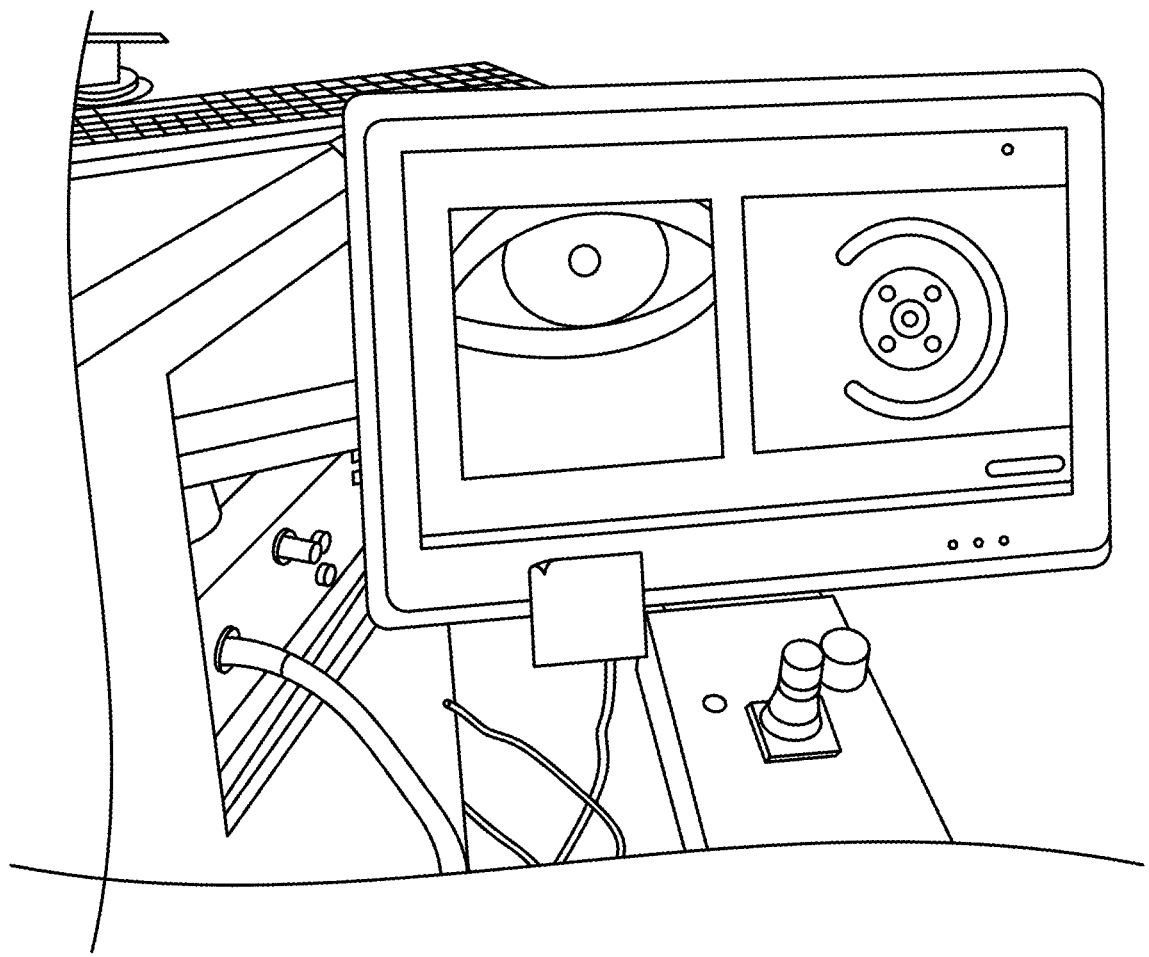
Figure 15:
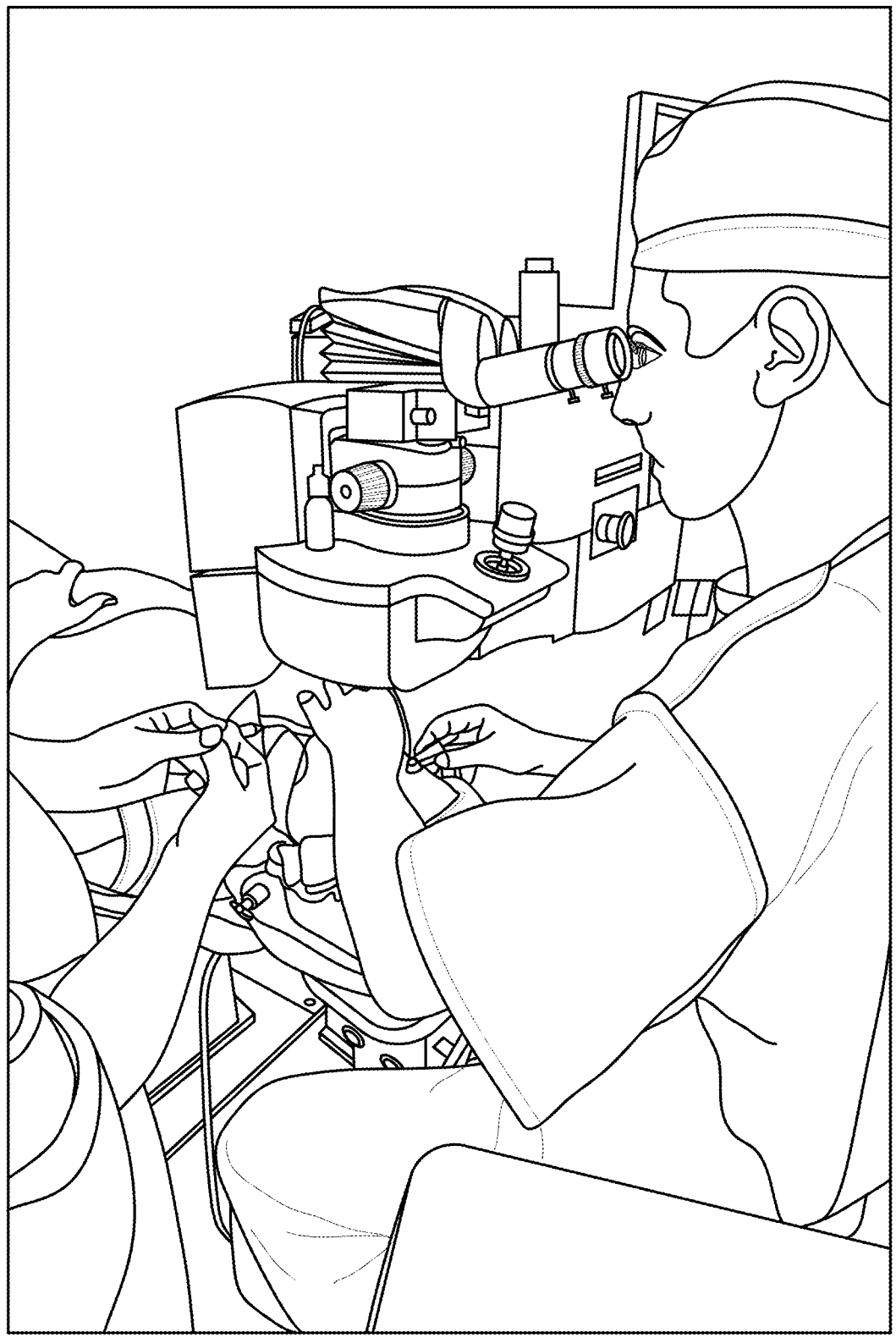
FIG. 15 depicts an example use case for cataract lasik surgery, in accordance with some example implementations.
Figure 16:
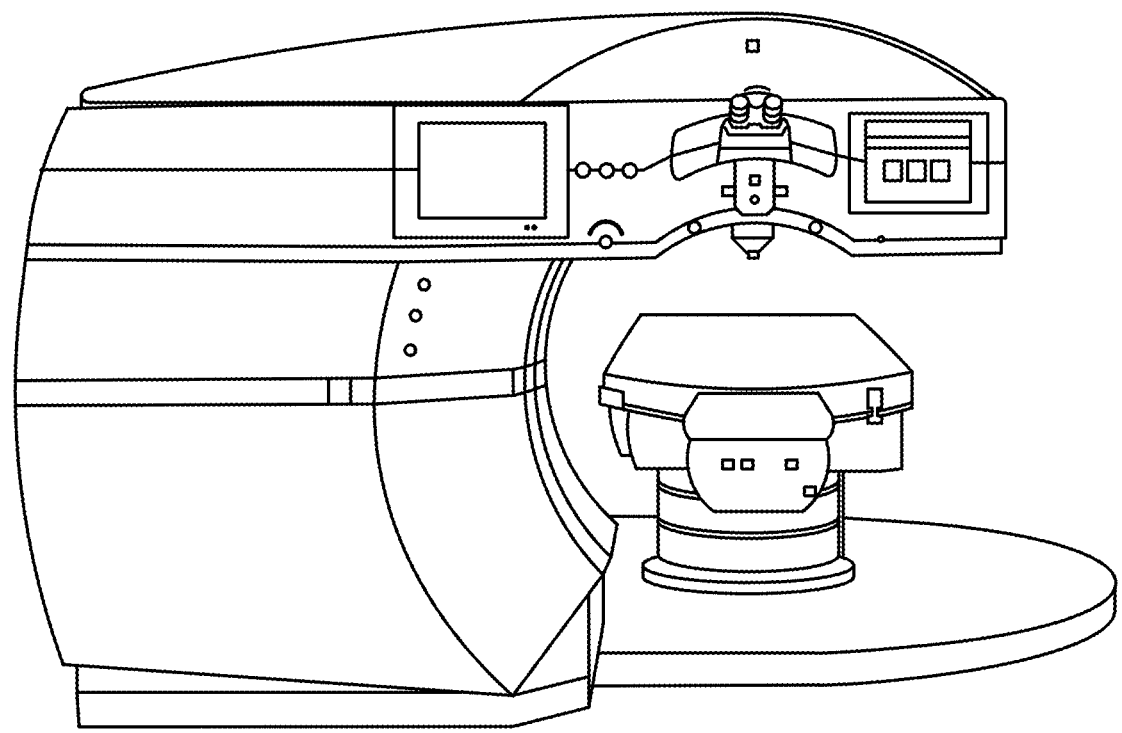
FIG. 16 depicts an example use case for femtosecond surgery, in accordance with some example implementations.
Figure 17:
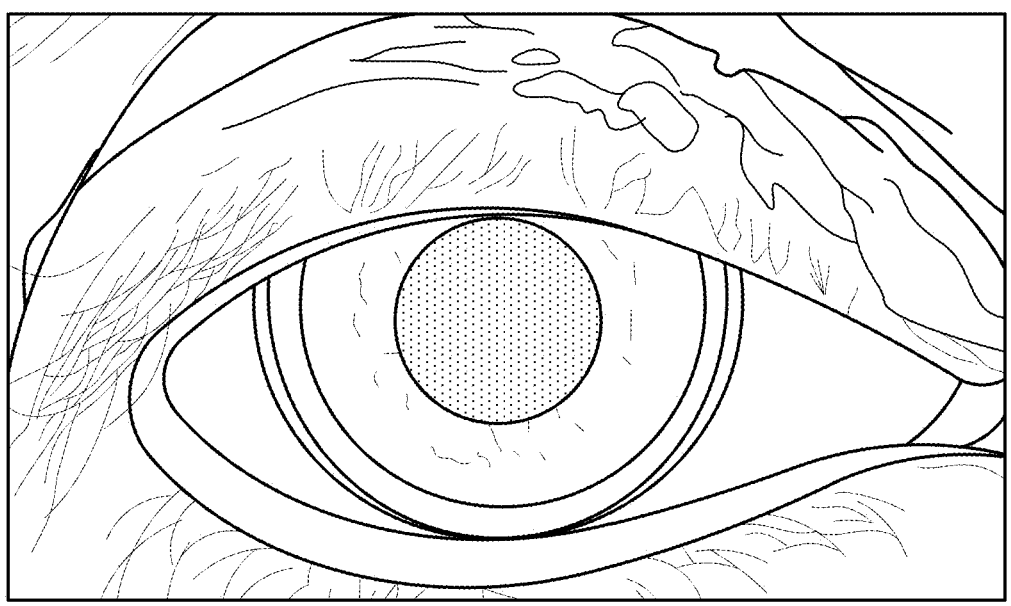
FIG. 17 depicts an example use case for cataract surgery, in accordance with some example implementations.
Figure 18:
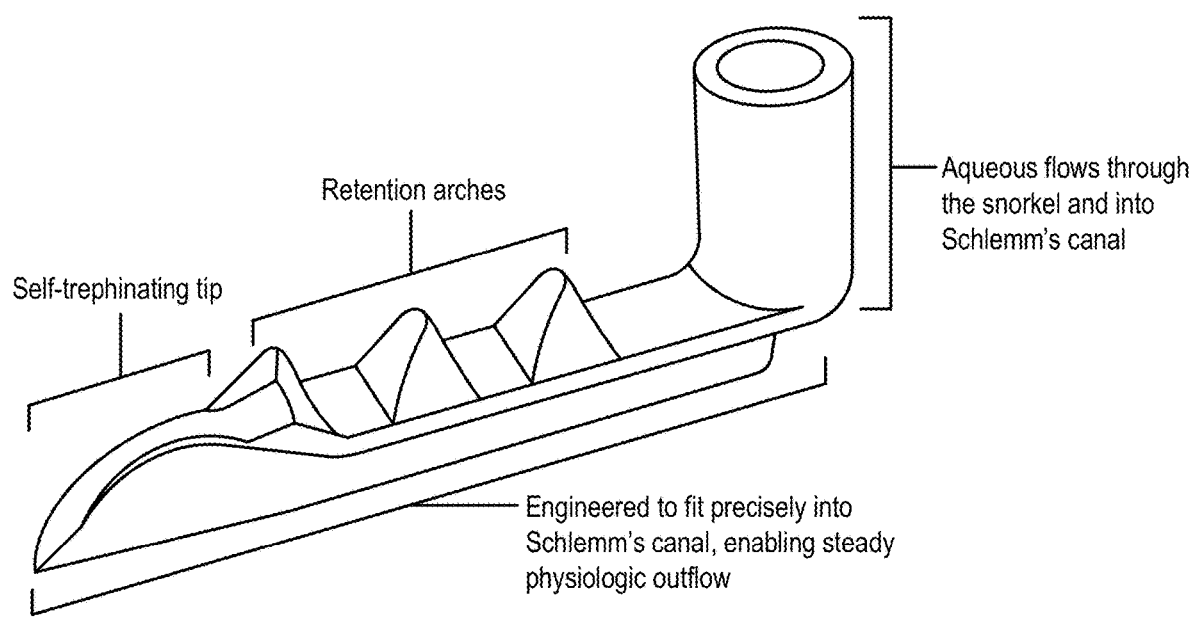
FIG. 18 depicts an example use case for a micro-invasive glaucoma surgery (MIGS) implant, in accordance with some example implementations.
Figure 19:
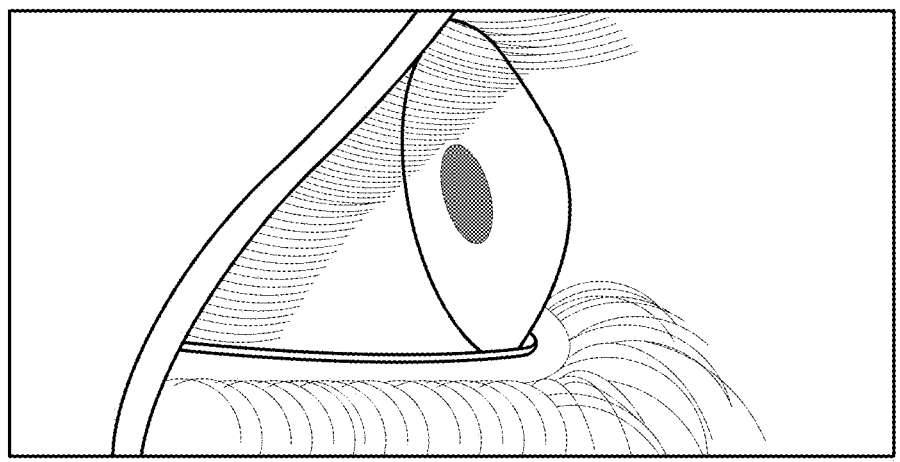
FIG. 19 depicts an example use case for keratoconus surgery, in accordance with some example implementations.
Figure 20:
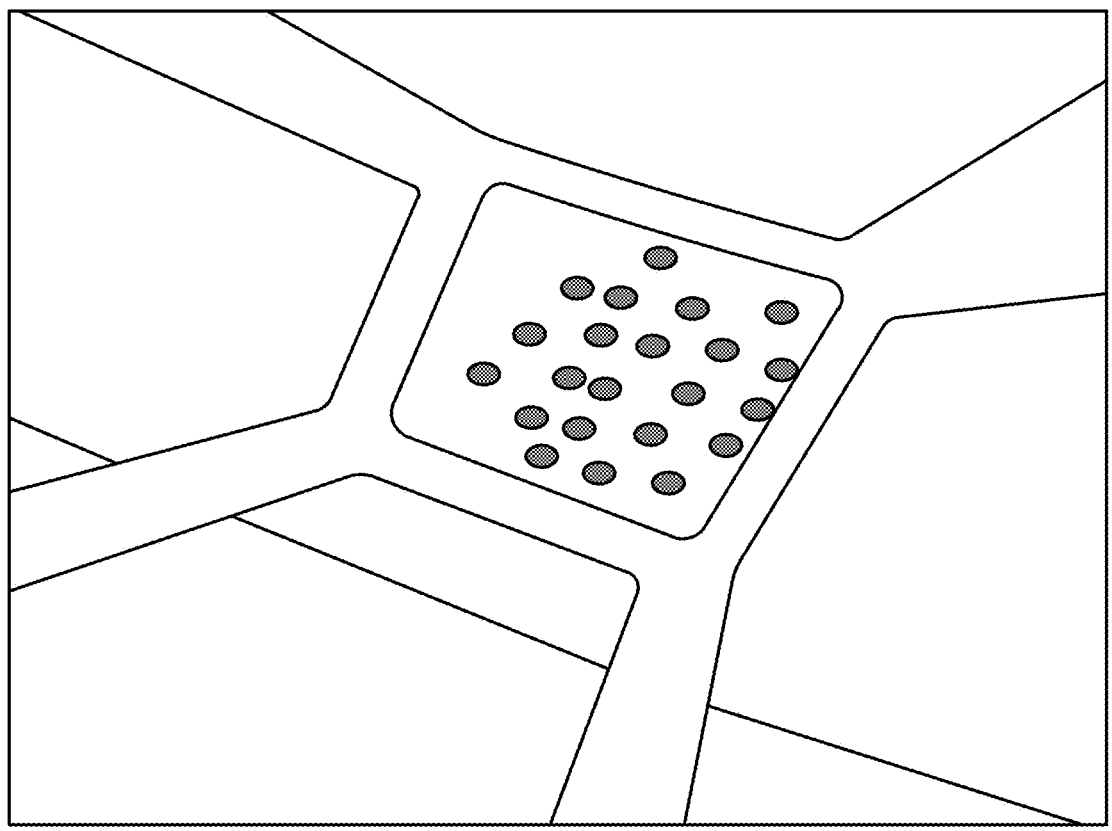
FIG. 20 depicts an example use case for laser scleral microporation.

The robotics assembly 110 can be used with a relational database, a neural network (e.g., neural network 875), or the like in order to provide feedback to and from the eye tracking system. This could allow the eye tracker and the eye movements of the robotics assembly 110 to be synchronized in real-time with bi-directional feedback. FIGS. 14A and 14B depict an example robotics assembly (e.g., robotics assembly 110) and an eye tracker, in accordance with some example implementations.

Natural or other human eye movement can be simulated with the robotics assembly 110 and/or the animatronics assembly 600 by using a neural network (e.g., neural network 875 or other AI) controller. Video images of natural human eye movement can be used as a training set for the AI system. Scoring can be accomplished through eye tracking or other external system and annotation. This would provide a high fidelity simulation natural eye movement by the robotic eye system (e.g., robotics assembly 110). Using an eye tracker on a live person, then the robotic eye simulator could mimic natural eye motion with either a direct or recorded connection.

Method 1300 can proceed to operational block 1320 where the apparatus 1200, for example, can connect to one or more computing devices. In some aspects, connecting to one or more computing devices can include connecting to a remote training environment (e.g., remote training environment 200). For example, a doctor (e.g., user 202) may sign into a group meeting (e.g., a video conference meeting) where an eye surgery training may be performed. In some aspects, other devices or users (e.g., a laser, a camera, computers, moderator, other physicians, or the like) may sign into the group meeting (e.g., remote training environment 200). The group meeting may allow the users 202 to communicate with each other and/or control one or more computing devices (e.g., the laser, the robotics assembly 110, the server 225, the client device 205, or the like) goal Connected to the most remote training environment. The one or more computing devices can include the client device 205, the server 225, the computing apparatus 1200, or the like. In some aspects, the remote training environment may include a connection to the robotics assembly and/or the laser for eye surgery.

Method 1300 can proceed to operational block 1330 where the apparatus 1200, for example, can operate, by the one or more computing devices, the robotics assembly. In some aspects, operating the robotics assembly can include performing a training treatment, a training surgery, a training procedure, a treatment planning, a post-treatment review, or the like. For example, a moderator (e.g., a physician trainer or instructor) may walk through a determined training exercise with a physician user (e.g., user 202). The moderator may give control to the robotics assembly 110 and/or the laser for eye surgery to the physician user for performing the determined training exercise. In some aspects, the determined training exercise may include performing a simulated surgery such as a cataract surgery, a cataract LASIK, a FemtoSecond surgery, an MIGS implant surgery, a Keratoconus surgery, Laser Scleral Microporation, or the like. FIGS. 15-20 depict example use case surgeries/procedures using a robotics assembly (e.g., robotics assembly 110), in accordance with some example implementations described herein. While certain surgeries/procedures are described and shown herein, the methods and apparatus for live, virtual or remote eye surgery training may apply to other surgeries, procedures, studies, etc.

Figure 21A:
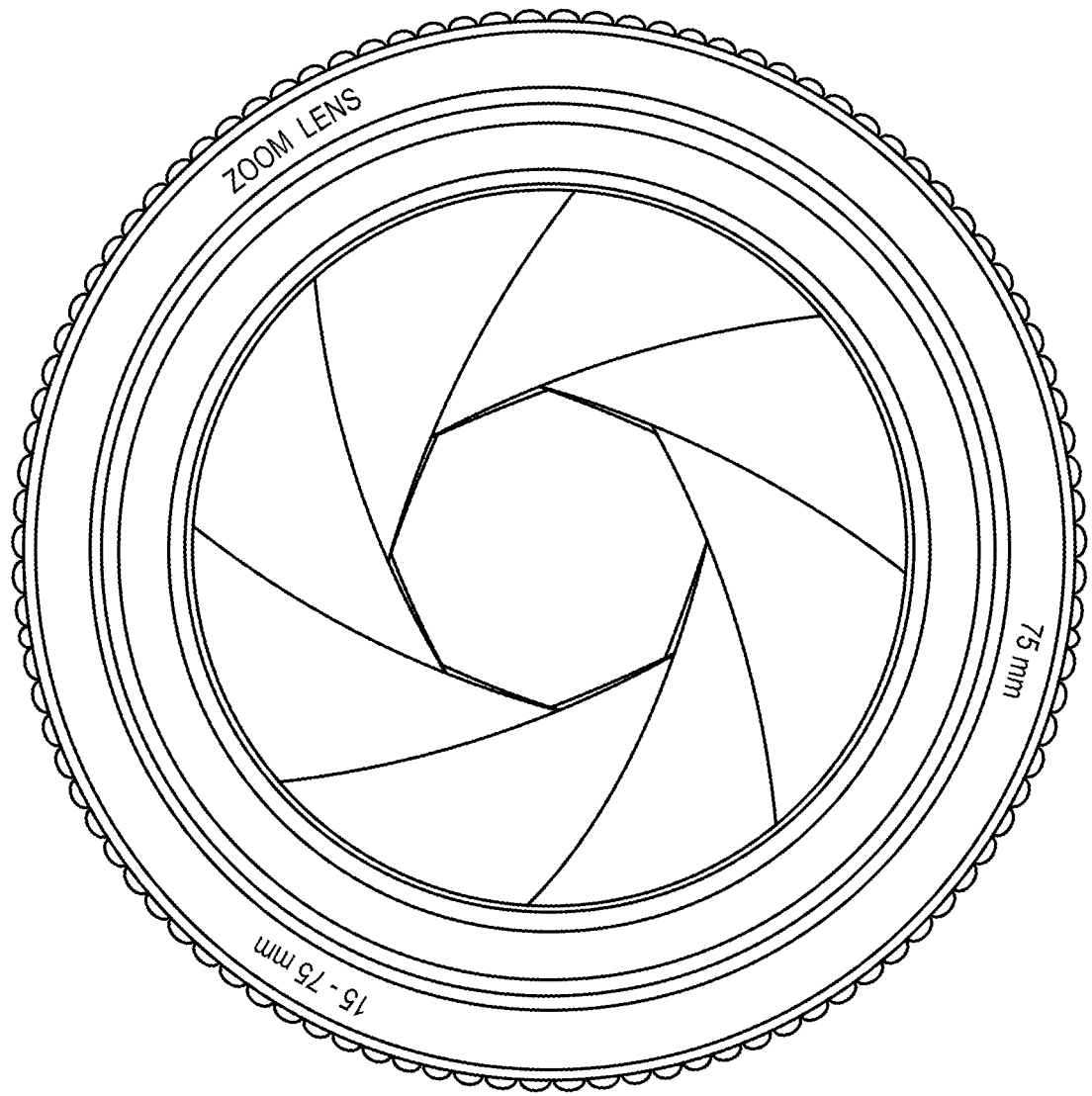
FIGS. 21A-21C show implementations of an iris shutter feature.
Figure 21B:
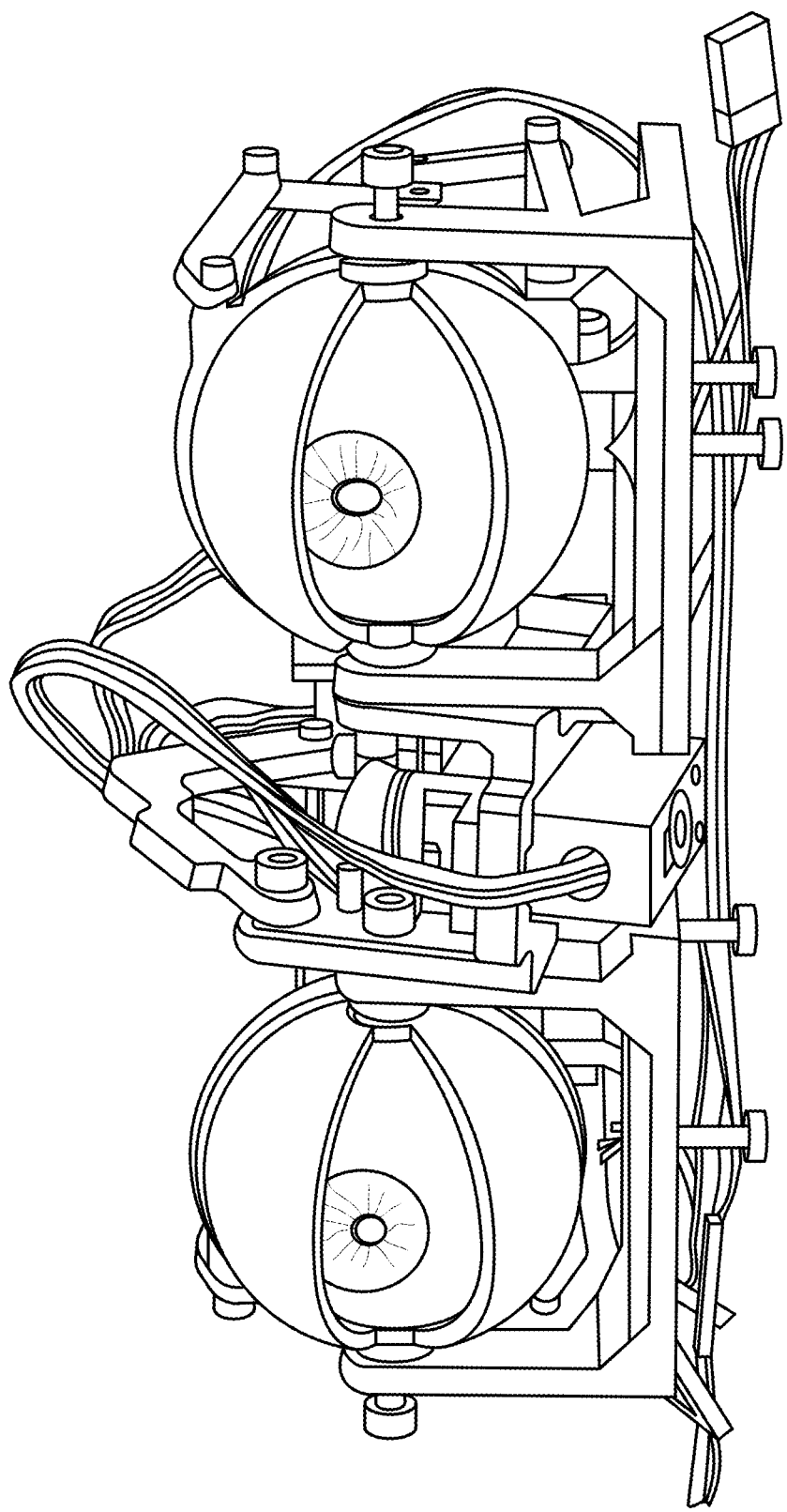
Figure 21C:
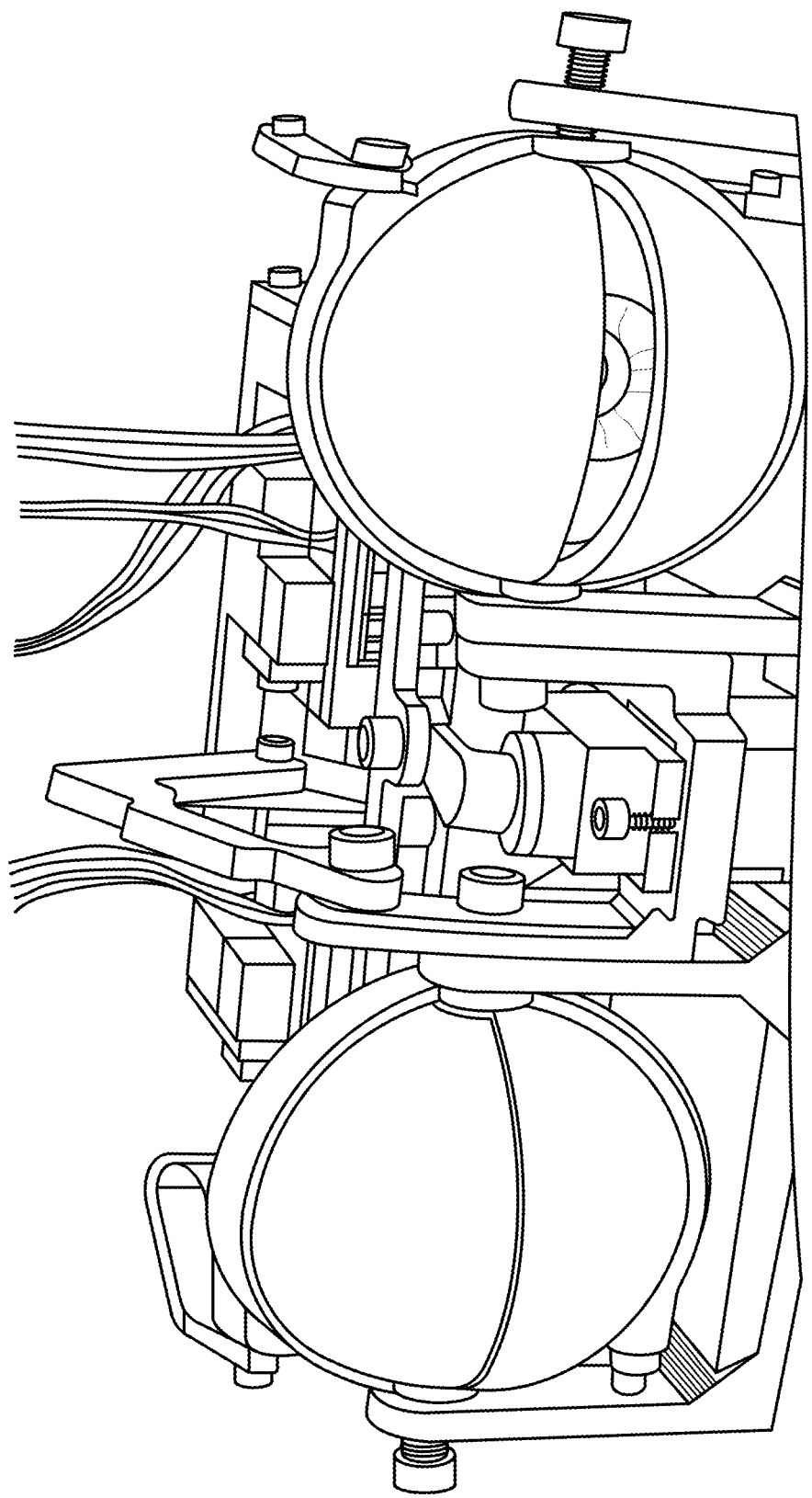
Figure 22:
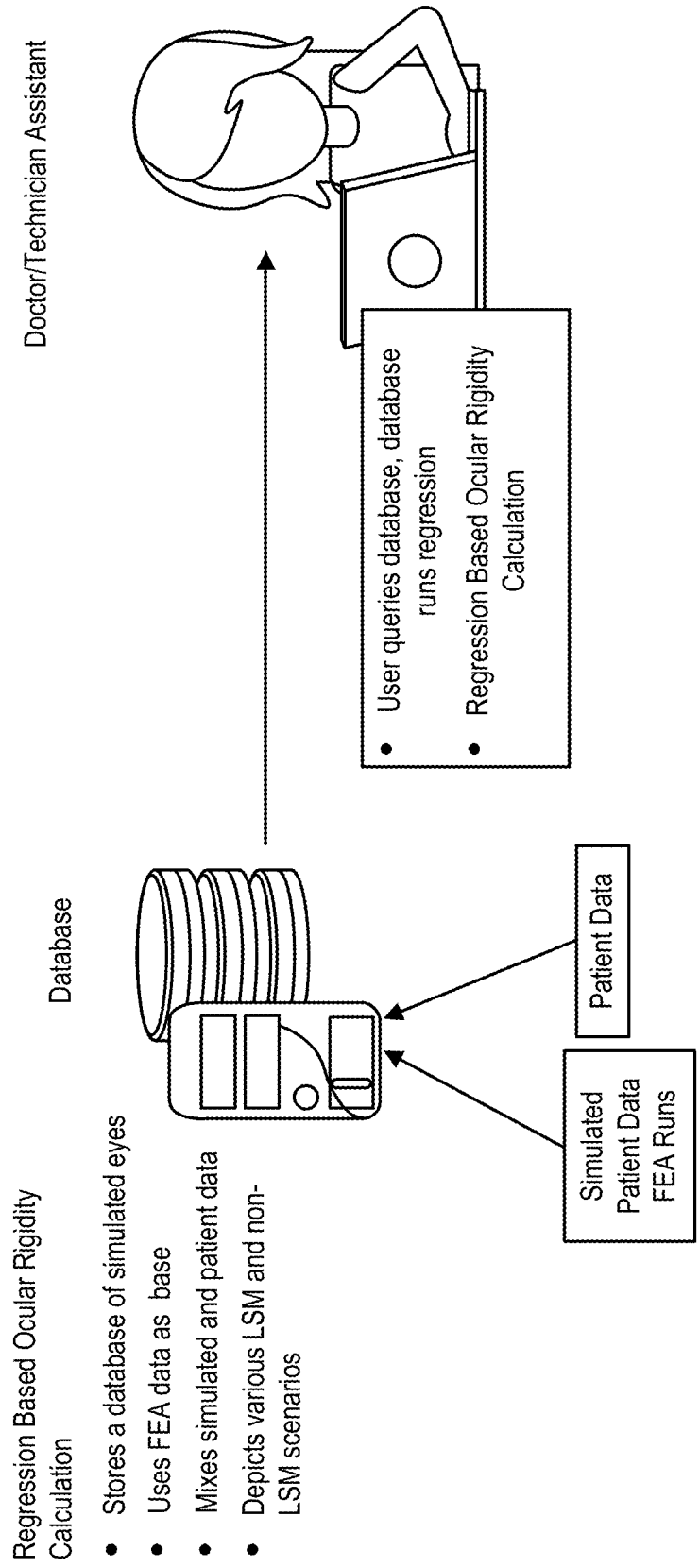
FIG. 22 shows a representation of a data repository and database which can communicate with a plurality of external inputs. The system can further collect telemetry data and produce outputs to various extremal device.

In some variations of the system, as shown in FIGS. 21A-21C, the system further includes an "iris" shutter which is mechanically responsive to various stimulation and light iterations. The system further can be mechanically fixed to a plurality of iris sizes. The system further is designed for contrast to allow the eye to work parallel to the function of a human or animal eye. The system further is designed so as to simulate a normal human eye function.

Method 1300 can proceed to operational block 1340 where the apparatus 1200, for example, can simulate a human or animal eye movement during the determined training exercise. Simulating the human or animal eye movement can include controlling movement of an eye of the robotics assembly 110. In some aspects, eye surgeries or eye procedures may include directing a human or animal to fixate their gaze or focus their eyes on an object in order to position the human or animal's eye in a desired location for the surgery or procedure (e.g., eyes looking forward, eyes looking to the right, eyes looking to the left, eyes looking up, eyes looking down, or the like). For example, controlling the movement of the eye may include directing the eye (e.g., eye 506) to look at a target displayed on a screen or other location (e.g., GUI 1000). In some aspects, controlling movement of the eye may include initiating a random jitter movement to the eye. Controlling the movement of the eye may include controlling the movement via a user interface (e.g., GUI 1000). Controlling the movement of the eye may include operating a controller (e.g., the controller 150).

Method 1300 can proceed to operational block 1350 where the apparatus 1200, for example, can operate the laser for eye surgery to perform the determined training exercise. Operating the laser for eye surgery may include using one or more lasers to reshape a portion of an eye (e.g., eye 506) of the robotics assembly. In some aspects, operating the laser may include determining the eye is in a desired position for the determined training exercise.

In some implementations, method 1300 can additionally or alternatively involve the apparatus 1200, for example, operating the robotics assembly to perform eye tracking verification, treatment angle verification, a screen calibration, lab development, wavefront measurements, eye measurements, retina treatments, simulated eye surgeries, or the like. In some aspects, eye tracking verification may include determining a focal point of the eye 506 using a laser. In some aspects, the eye holder (e.g., the eye holder 502) may beneficially provide depth control of the eye 506 within the holder 502. For example, the eye holder 502 may allow modifications to a position of the eye 506 within the folder 502. In some aspects, the method 1300 may include performing a post-treatment review or post-exercise review, where results of the training exercise may be measured and analyzed.

Eye tracking and/or eye tracking verification may include using an onboard camera to track the position of one or more eyes 506. The eye tracking data may be inputted into an artificial intelligence (AI) feedback loop (e.g., neural network 875) to interpret the data and determine the position of the one or more eyes 506. In some aspects, a laser may be placed in the eye holder 502 to simulate a focal point or gaze of the one or more eyes 506 disposed in the eye holder 502. One or more mirrors may be positioned to reflect a laser beam and represent an angle of the eye movement of the one or more eyes 506. A target for a desired location may be selected for where a human or animal should be looking. When the eye 506 is moved to the correct position, the laser beam may be reflected off the mirror and hit the target at the desired location. The position may be recorded and the coordinates for the X and Y axis may be stored in memory.

Performance of the method 1300 and/or a portion thereof can allow for improved real-life, realistic simulation and training physicians for eye surgeries. For example, settings and/or modes of the robotic assembly 110 can simulate dynamic real-time and realistic eye movement of a human or animal (e.g., a directed gaze mode, a flutter a jitter mode, a human mode, etc.).

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code; include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a joystick, touchscreen, voice command processor, mouse or a trackball, by which the user may provide input to the computer. Other kinds of devices can be used to provide for interaction with a user as well. For example, feedback provided to the user can be any form of sensory feedback, such as for example visual feedback, auditory feedback, tactile feedback, data feedback, digital feedback, virtual feedback, or the like; and input from the user may be received in any form, including acoustic input, speech input, tactile input, and/or the like. Other possible input devices include touch screens or other touch-sensitive devices such as single or multi-point resistive or capacitive trackpads, voice recognition hardware, software, computational circuits, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such phrases are intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." The use of the term "based on,"

above and in the claims is intended to mean "based at least in part on," such that a feature or element that is not recited is also permissible.

The illustrated methods are exemplary only. Although the methods are illustrated as having a specific operational flow, two or more operations may be combined into a single operation, a single operation may be performed in two or more separate operations, one or more of the illustrated operations may not be present in various implementations, and/or additional operations which are not illustrated may be part of the methods. In addition, the logic flows depicted in the accompanying figures and/or described herein do not necessarily require the particular order shown, or sequential order, to achieve desirable results. Other implementations may be within the scope of the following claims.

What is claimed is:

1. A method comprising:
   initializing, by a processor, a robotics assembly;
   connecting, by the processor, the robotics assembly to one or more computing devices;
   operating, by the processor, the robotics assembly;
   simulating, by the processor, an eye movement of a human or animal, wherein the simulating includes:
      highlighting, visualizing, diagnosing & treating, via a user interface of the one or more computing devices, certain areas of the eye, and
      dynamic real-time realistic movement of the eye in response to controls on the user interface.

2. A system comprising:
   a base plate;
   a face plate coupled to the base plate;
   a controller electronically connected to at least one processor and configured to receive an input to control a position of the eye;
   an eye holder disposed within the face plate;
   an interface board configured to provide an electronic connection between the at least one processor and the eye holder;
   an eye disposed in the eye holder;
   a user interface configured to receive a user input to control a movement of the eye; and
   the at least one processor coupled to the base plate;
   wherein the at least one processor is configured to:
      initialize a position of the eye;
      connect to one or more computing devices or mobile or wearable devices;
      control, by the one or more computing devices, mobile or wearable devices, the position of the eye;
      simulate an eye movement of a human or animal; and
      perform a laser procedure on the eye.

3. The system of claim 1, wherein the system further comprises a laser.

4. The system of claim 1, wherein the eye holder comprises of an apparatus that initializes, monitor, adjust, and measure intraocular pressure inside the eye.

5. The system of claim 1, wherein the eye holder comprises a suction cup controlled by the user interface.

6. The system of claim 1, wherein the face plate is removable and in the shape of an animal species or human.

7. A method comprising:
   initializing, by a processor, a robotics assembly;
   installing an eye into an eye holder of the robotics assembly;
   connecting, by the processor, to one or more computing devices;
   operating, by the processor, the robotics assembly;
   simulating, by the processor, an eye movement of a human or animal; and
   operate, by the processor, a laser to perform a determined exercise on an eye of the robotics assembly, wherein the determined exercise comprises an eye measurement.

8. The method of claim 7, wherein the determined exercise further comprises a simulated cataract surgery, a simulated LASIK surgery, a simulated retina treatment, or a Scleral procedure a vision treatment.

9. The method of claim 7, wherein simulating the eye movement comprises controlling the movement via a user interface.

10. The method of claim 7, wherein the eye holder of the robotics assembly initializes intraocular pressure inside the eye.

11. The method of claim 10, wherein the eye comprises one of a glass eye, a wooden eye, a cadaver eye, an animal eye, phatom material and an artificial eye.

12. The method of claim 9, wherein the user interface comprises one or more modes to simulate a real human or animal eye movement or abnormal movements.

13. The method of claim 10, wherein the eye holder changes a pressure in the eye.

14. The method of claim 7, further comprising tracking a position of the eye.

15. The method of claim 14, further comprising verifying, in response to the tracking, the position matches a target position and fixation on a target via a feedback loop.

16. The method of claim 14, further comprising a blink mechanism and an iris shutter, simulating real life eye functions.

17. The method of claim 11, wherein the eye holder of the robotics assembly monitors intraocular pressure inside the eye.

18. The method of claim 17, wherein the eye holder of the robotics assembly adjusts intraocular pressure inside the eye.

19. The method of claim 18, wherein the eye holder of the robotics assembly measures intraocular pressure inside the eye.

20. The method of claim 7, wherein the eye holder changes a position of the eye within the eye holder.

21. The method of claim 20, wherein the eye holder is a suction cup.

22. The method of claim 21, wherein the eye holder includes a lip configured to hold a rubber dental dam.

* * * * *